United States Patent
Mori

(10) Patent No.: US 10,406,041 B2
(45) Date of Patent: Sep. 10, 2019

(54) UNDERPANTS-TYPE DISPOSABLE DIAPER

(71) Applicant: DAIO PAPER CORPORATION, Ehime (JP)

(72) Inventor: Yosuke Mori, Ehime (JP)

(73) Assignee: Daio Paper Corporation, Ehime (JP)

( * ) Notice: Subject to any disclaimer, the term of this patent is extended or adjusted under 35 U.S.C. 154(b) by 318 days.

(21) Appl. No.: 15/119,612

(22) PCT Filed: Feb. 26, 2015

(86) PCT No.: PCT/JP2015/055557
§ 371 (c)(1),
(2) Date: Aug. 17, 2016

(87) PCT Pub. No.: WO2015/137127
PCT Pub. Date: Sep. 17, 2015

(65) Prior Publication Data
US 2017/0049637 A1    Feb. 23, 2017

(30) Foreign Application Priority Data

Mar. 12, 2014 (JP) .................................. 2014-049110

(51) Int. Cl.
*A61F 13/493* (2006.01)
*A61F 13/496* (2006.01)
(Continued)

(52) U.S. Cl.
CPC .......... *A61F 13/493* (2013.01); *A61F 13/496* (2013.01); *A61F 13/49011* (2013.01);
(Continued)

(58) Field of Classification Search
CPC ................ A61F 13/49; A61F 13/49007; A61F 13/49011; A61F 13/49012;
(Continued)

(56) References Cited

U.S. PATENT DOCUMENTS

| | | | | |
|---|---|---|---|---|
| 6,632,211 B2 * | 10/2003 | Otsubo | ................ | A61F 13/496 604/385.16 |
| 6,648,868 B2 * | 11/2003 | Sayama | ............ | A61F 13/49019 604/385.22 |
| 6,808,516 B2 * | 10/2004 | Tsuji | ................. | A61F 13/49017 604/385.25 |
| 6,991,623 B2 * | 1/2006 | Tanaka | ............... | A61F 13/49019 604/385.01 |

(Continued)

FOREIGN PATENT DOCUMENTS

| | | |
|---|---|---|
| JP | 7-163618 A | 6/1995 |
| JP | 2005-279077 A | 10/2005 |

(Continued)

*Primary Examiner* — Catherine L Anderson
(74) *Attorney, Agent, or Firm* — Muncy, Geissler, Olds & Lowe, P.C.

(57) ABSTRACT

To enable producing without the need for an extension step of an outer body while being excellent in a fit of the edges around the legs. The above problem is solved by an underpants-type disposable diaper wherein an inner body is joined to a crotch side edge portion of a central portion in a width direction of a dorsal side outer body to form an inner body joined section, a front-back length of a side closer to a waist side than the inner body joined section is extensible to a crotch side, and the side closer to the waist side than the inner body joined section in the inner body can be moved to the crotch side, relative to a dorsal side outer body.

8 Claims, 38 Drawing Sheets

(51) Int. Cl.
  *A61F 13/49*  (2006.01)
  *A61F 13/494* (2006.01)
  *A61F 13/514* (2006.01)
  *A61F 13/534* (2006.01)
  *A61F 13/539* (2006.01)
  *A61F 13/56*  (2006.01)
  *A61F 13/53*  (2006.01)

(52) U.S. Cl.
  CPC .. *A61F 13/49406* (2013.01); *A61F 13/51476* (2013.01); *A61F 13/534* (2013.01); *A61F 13/539* (2013.01); *A61F 13/5655* (2013.01); *A61F 2013/5349* (2013.01); *A61F 2013/530481* (2013.01)

(58) Field of Classification Search
  CPC ............ A61F 13/49058; A61F 13/4906; A61F 13/49061; A61F 13/493; A61F 13/49406; A61F 13/496; A61F 13/539; A61F 2013/49031; A61F 2013/49053; A61F 2013/49098
  See application file for complete search history.

(56) References Cited

U.S. PATENT DOCUMENTS

| | | | |
|---|---|---|---|
| 9,668,925 B2* | 6/2017 | Mukai | A61F 13/496 |
| 2002/0147439 A1* | 10/2002 | Tanaka | A61F 13/496 604/398 |
| 2004/0002689 A1* | 1/2004 | Igaue | A61F 13/49012 604/385.01 |
| 2005/0107764 A1 | 5/2005 | Matsuda et al. | |
| 2011/0288517 A1 | 11/2011 | Mori | |

FOREIGN PATENT DOCUMENTS

| | | |
|---|---|---|
| JP | 2007-511326 A | 5/2007 |
| JP | 2008-036019 A | 2/2008 |
| JP | 2008-178682 A | 8/2008 |
| JP | 2010-162277 A | 7/2010 |
| JP | 2010-184134 A | 8/2010 |
| JP | 2012-061167 A | 3/2012 |
| JP | 2012-239555 A | 12/2012 |
| JP | 2014-004492 A | 1/2014 |

* cited by examiner

Cross section at 6-6

Cross section at 6-6

Cross section at 7-7

Cross section at 7-7

Cross section at 6-6

Cross section at 6-6

Cross section at 7-7

Cross section at 7-7

Cross section at 6-6

Cross section at 7-7

Cross section at 6-6

Cross section at 7-7

UNDERPANTS-TYPE DISPOSABLE DIAPER

TECHNICAL FIELD

The present invention relates to an underpants-type disposable diaper.

BACKGROUND ART

As one aspect of an underpants-type disposable diaper, there has been known an underpants-type disposable diaper including an outer body formed in a cylindrical shape by joining both side portions of a ventral side outer body and both side portions of a dorsal side outer body and an inner body that is provided from a central portion of an inner surface of the ventral side outer body in a width direction to a central portion of an inner surface of the dorsal side outer body in a width direction, and absorbs excretion, wherein the ventral side outer body and the dorsal side outer body are not continuous but separated from each other on the crotch side (refer to Patent Documents 1 to 4). Such an outer halved type has the advantage that no leg openings for passage of the user's legs need to be punched or only small-area leg openings need to be punched. That is, there is the advantage that when cut pieces (hereinafter also referred to as trims) are discarded, the material loss resulting from the trims (hereinafter also referred to as trim loss) can be suppressed.

However, any attempts to completely eliminate the trim loss would disable the formation of the edges of the leg openings along the peripheries of the groin region and the buttocks. Accordingly, taking the fit around the legs into consideration, even the outer halved type could not enable complete elimination of the trim loss.

As a solution of this problem, there has been proposed an underpants-type disposable diaper, wherein by configuring an outer body to be extensible to a crotch side, and extending (increasing the width of) a central portion of the outer body in a width direction to the crotch side relative to both sides thereof during manufacturing, edges of the leg openings in the outer body positioned in the lateral sides of the inner body obliquely face up to side edge portions, and the edges of the leg openings are formed along the peripheries of the groin region and the buttocks (Refer to Patent Documents 3 and 4).

In the related art, however, there still remains a problem that an extension step is needed during manufacturing.

CITATION LIST

Patent Document

Patent Document 1: JP-T No. 2007-511326
Patent Document 2: JP-A No. 2005-279077
Patent Document 3: JP-A No. 2010-162277
Patent Document 4: JP-A No. 2014-4492

SUMMARY OF INVENTION

Problems to be Solved by the Invention

A major object of the present invention is to provide an underpants-type disposable diaper of an outer halved type that can be produced without the need for the extension step of an outer body, while providing an excellent fit of the edges around the legs.

Means for Solving the Problem

The present invention as a solution to the foregoing problem is as follows:

The Invention of Claim 1

An underpants-type disposable diaper, comprising:
an outer body having a ventral side outer body and a dorsal side outer body, side edge portions of the ventral side outer body and side edge portions of the dorsal side outer body being joined at both sides in a width direction to form a waist opening; and
an inner body extended from a central area of the ventral side outer body in the width direction to a central area of the dorsal side outer body in the width direction so as to pass through a wearer's crotch,
wherein in the outer body of at least one side of the ventral side outer body and the dorsal side outer body, a crotch side edge portion of a central portion in the width direction is joined with the inner body to form an inner body joined section, and a length in a front-back direction of a side in the outer body closer to the waist than to the inner body joined section is extensible to a crotch side, and
a portion of the inner body disposed closer to the waist than to the inner body joined section can be moved to the crotch side, relative to the outer body of the at least one side.

Operation and Effect

In this invention, the length in the front-back direction of the side in the outer body closer to the waist than to the inner body joined section is extensible to the crotch side while the inner body is moved to the crotch side relative to the outer body, so that the edges of the leg openings of the outer body positioned in lateral sides of the inner body obliquely face up to the side edge portions, and the shapes of the edges of the leg openings are formed to fit around buttocks and a groin region. Such deformation can be made not only manually when the product is used, but also naturally when the diaper is pulled up to the waist and attached, or by force (for example, in a diaper where the resilient and elastic member is built-in to improve the fit, the contraction force thereof, or force of gravity applied to the inner body) applied to the diaper after producing. Therefore, the diaper has excellent fit of the edges around the legs at least in the worn state. In addition, the diaper can be produced without the need for the extension step of the outer body.

The Invention of Claim 2

The underpants-type disposable diaper, according to claim 1, wherein
a part of the outer body of the at least one side disposed at the crotch side is folded in the front-back direction once or a few times in a zigzag manner, both lateral side end portions of the crotch side portion are fixed in a folded state to constitute non-unfolded parts, and a part between the non-unfolded parts is unfixed and unfolded, so that a folded part is formed,
the inner body is joined to a portion of the folded part disposed closer to a forward edge than to a fold closest to the forward edge to form the inner body joined section,
in the folded part, an elongated resilient and elastic member is provided, which is fixed in an extended state along the width direction and which is in an oblique direction when the diaper is worn while the folded part is folded over an entire width direction, and the folded part is unfolded so that the length in the front-back direction of the side in the outer body closer to the waist than to the inner body joined section is extensible to the crotch side.

Operation and Effect

An extensible structure of the outer body being configured by such a folded part, the edges of the leg openings of the outer body positioned in the lateral sides of the inner body obliquely face up to the side edge portions when the diaper is worn. In addition, since the contraction force of the oblique resilient and elastic member acts along the edges of the leg openings, these edges closely fit well around the wearer's buttocks and groin region.

The Invention of Claim 3

The underpants-type disposable diaper according to claim 1, wherein in the side in the outer body closer to the waist than to the inner body joined section, a separation portion composed of a slit or an elongated opening is provided so as to extend in the width direction from one side to another side of a center in the width direction, in the crotch side of the separation portion, an elongated resilient and elastic member, which is fixed in an extended state along the width direction and which is in an oblique direction when the diaper is worn, is provided and a portion disposed at the crotch side of the separation portion is deformed to separate in relation to a portion disposed at a waist side of the separation portion to the crotch side so that the length in the front-back direction of the side in the outer body closer to the waist than to the inner body joined section is extensible to the crotch side.

Operation and Effect

With the extensible structure of the outer body being configured by such a separation portion, the edges of the leg openings of the outer body positioned in the lateral sides of the inner body obliquely face up to the side edge portions when the diaper is worn. In addition, since the contraction force of the oblique resilient and elastic member acts along the edges of the leg openings, these edges closely fit well around the wearer's buttocks and groin region. Further, since the structure is so simple that only the slit or the like is provided, there is no increase in the material cost and producing is easy.

The Invention of Claim 4

The underpants-type disposable diaper according to claim 1, wherein the outer body of the at least one side has extensibility at least in the front-back direction so that the length in the front-back direction of the side in the outer body closer to the waist than to the inner body joined section is extensible to the crotch side.

Operation and Effect

With the extensible structure of the outer body being thus realized by the extensibility of the outer body itself, the edges of the leg openings of the outer body positioned in the lateral sides of the inner body obliquely face up to the side edge portions when the diaper is worn, and the edges of the leg openings fit around the wearer's buttocks and groin region. In addition, this can be implemented only by changing a sheet material.

The Invention of Claim 5

The underpants-type disposable diaper according to any one of claims 1 to 4, wherein the inner body is extended only to the crotch side edge portion of the outer body of the at least one side, on the outer body of the at least one side.

Operation and Effect

By making the moving portion short in the side in the outer body closer to the waist than to the inner body joined section, unintentional deformation such as bend and turn-up of the moving portion can be prevented. In particular, a structure having short length of the inner body in a dorsal side outer body side is suitable for a product that requires less absorption performance on the dorsal side, such as training pants for infants and incontinence pants for male users.

The Invention of Claim 6

The underpants-type disposable diaper according to any one of claims 1 to 4, wherein the inner body has a moving portion extended in a side of the inner body closer to the waist than to the inner body joined section in the outer body of the at least one side, and a pressing belt is provided so as to extend across the inner body in the width direction in the side in the outer body of the at least one side closer to the waist than to the inner body joined section and so as to have portions, which are positioned at both sides of the moving portion of the inner body in the width direction to be fixed and a portion, which is passed over the moving portion of the inner body to be unfixed.

Operation and Effect

With such a pressing belt, the moving portion of the inner body can be held down so as not to move unnecessarily or excessively, thereby enabling prevention of unintentional deformation such as bend and turn-up of the moving portion.

The Invention of Claim 7

The underpants-type disposable diaper according to any one of claims 1 to 4, wherein the inner body has a moving portion extended in a side of the inner body closer to the waist than to the inner body joined section in the outer body of the at least one side, and a connecting belt is provided so as to extend across a waist side end portion of the inner body in the width direction in the side in the outer body of the at least one side closer to the waist than to the inner body joined section and so as to have portions, which are positioned at both sides of the moving portion of the inner body in the width direction to be fixed and the waist side end portion of the inner body is connected to the connecting belt.

Operation and Effect

With such a connecting belt, by limiting movement of the moving portion of the inner body to an extent allowed by looseness or sag of the connecting belt, the moving portion of the inner body can be prevented from moving unnecessarily or excessively, thereby enabling prevention of unintentional deformation such as bend and turn-up of the moving portion.

The Invention of Claim 8

The underpants-type disposable diaper according to any one of claims 1 to 4, wherein the inner body has a moving portion extended in a side of the inner body closer to the waist than to the inner body joined section in the outer body of the at least one side, and a waist flap is provided so as to protrude from an inner surface of a waist edge portion of the outer body of the at least one side and the moving portion of the inner body is extended and connected to the waist flap.

Operation and Effect

Thus, with ends of the moving portion of the inner body connected to the waist flap projecting from the inner surface of the waist edge portion of the outer body, by limiting movement of the moving portion of the inner body to an extent allowed by sag of free edges of the outer body, the moving portion of the inner body can be prevented from moving unnecessarily or excessively, thereby enabling prevention of unintentional deformation such as bend and turn-up of the moving portion.

The Invention of Claim 9

The underpants-type disposable diaper according to any one of claims 1 to 4, wherein the inner body has a moving portion extended in a side of the inner body closer to the waist than to the inner body joined section in the outer body of the at least one side, and in a site overlapping the moving portion in the outer body of the at least one side, a slip stopper is provided having an effect in a direction toward the crotch is weaker than effects in any other directions.

Operation and Effect

With such a slip stopper, the moving portion of the inner body can be held down so as not to move unnecessarily or excessively, while enabling extension of the outer body, thereby enabling prevention of unintentional deformation such as bend and turn-up of the moving portion.

Advantageous Effects of Invention

As described above, the present invention produces an advantage that it is possible to produce diapers without the need for an extension step of an outer body, while providing an excellent fit of the edges to around the legs.

DESCRIPTION OF EMBODIMENTS

Figure 1:
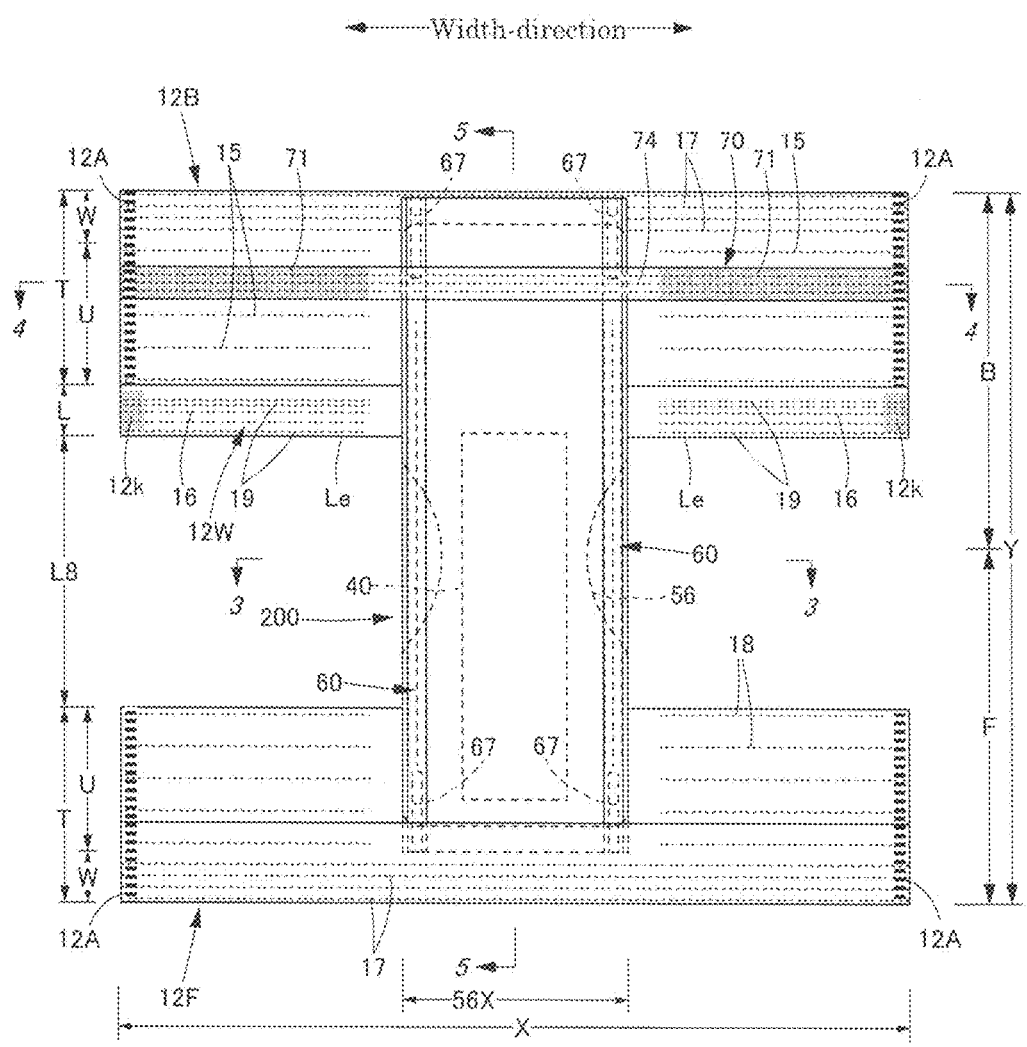
FIG. 1 is a planar view of an inner surface of an underpants-type disposable diaper in the open state.

One embodiment of the present invention will be described below with reference to the accompanying drawings.

<First Embodiment of an Underpants-Type Disposable Diaper>

FIGS. 1 to 10(*a*) illustrate one example of an underpants-type disposable diaper. In this underpants-type disposable diaper, both side edges of a ventral side outer body 12F in a width direction and both side edges of a dorsal side outer body 12B in the width direction are joined along a vertical direction by heat sealing, ultrasonic welding, or the like to form cylindrical-shaped outer bodies 12F and 12B. In addition, on the outer bodies 12F and 12B, a front end portion of an inner body 200 is connected by a hot-melt adhesive or the like to an inner surface of a central portion of the ventral side outer body 12F in the width direction, and a back end portion of the inner body 200 is connected by the hot-melt adhesive or the like to the inner surface of a central portion of the dorsal side outer body 12B in the width direction. Reference sign 12A indicates a joined section (side seal portion) of the ventral side outer body 12F and the dorsal side outer body 12B. In addition, reference sign Y indicates the entire length (vertical length from an edge of a waist opening in the front panel F to an edge of the waist opening in the back panel B) of the diaper in the open state, and reference sign X indicates the entire width of the diaper in the open state.

The inner body 200 is a part absorbing and retaining excretion such as urine, and the outer bodies 12F and 12B are parts for supporting the inner body 200 for the wearer's body. The dot patterns in the drawing represent a hot-melt adhesive for joining the constituent members. Alternatively, the members may be joined by welding process (heat sealing or ultrasonic sealing). The hot-melt adhesive may be applied in a solid, bead, curtain, summit, or spiral pattern. Instead of or in addition to this, for fixation of the resilient and elastic members, the hot-melt adhesive may be applied to the outer peripheral surface of the resilient and elastic members by the means of a comb gun or a Sure-Wrap application means.

Figure 2:
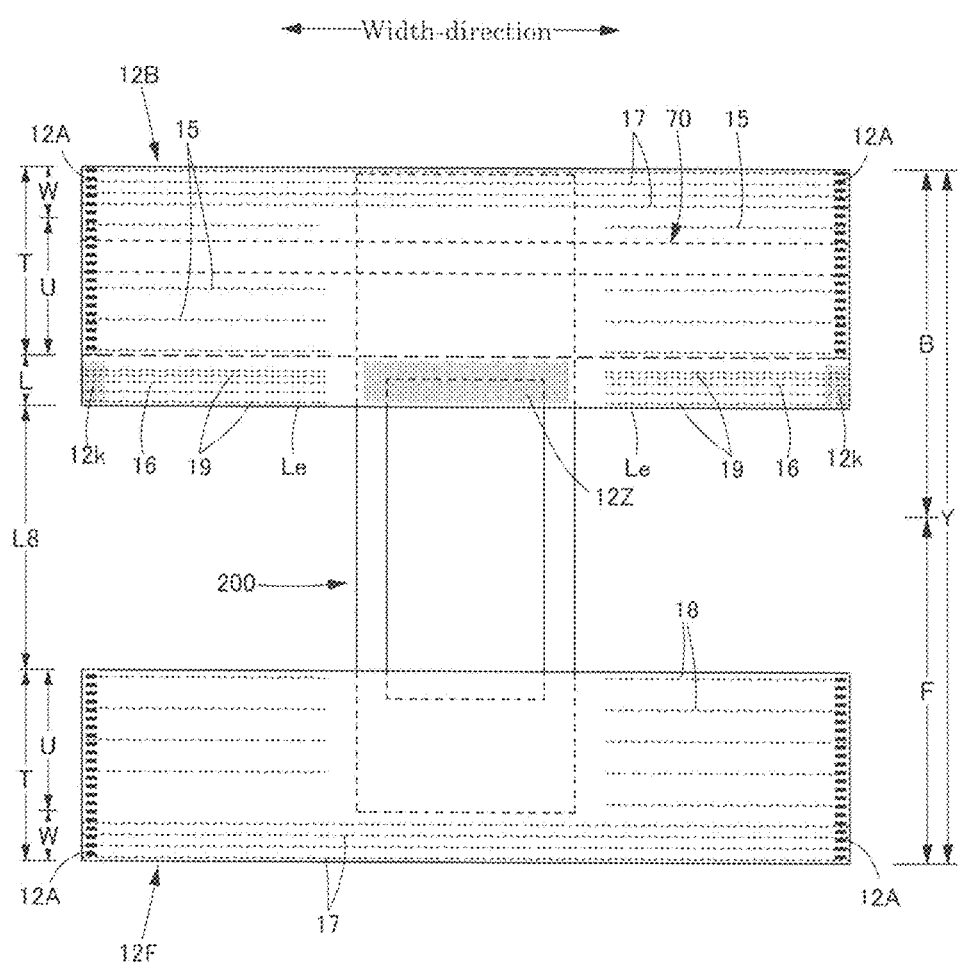
FIG. 2 is a planar view of an outer surface of the underpants-type disposable diaper in the open state.

The upper opening of the outer bodies 12F and 12B constitutes a waist opening through which the wearer's waist is passed. Parts surrounded, respectively, by lower edges of the outer bodies 12F and 12B and side edges of the inner body 200 at both sides of the inner body 200 in the width direction constitute leg openings through which the wearer's legs are passed. With respective welded portions 12A taken off and the outer bodies 12F and 12B opened, the inner body 200 has a narrower shaped intermediate portion in the front-back direction, as illustrated in FIGS. 1 and 2. The inner body 200 extends from the dorsal side to the ventral side, passing through and covering the crotch portion. The inner body 200 is a portion receiving and absorbing excretion and retaining the liquid thereof, and the outer bodies 12F and 12B are portions to support the inner body 200 to the wearer.

(Inner Body)

Figure 3:
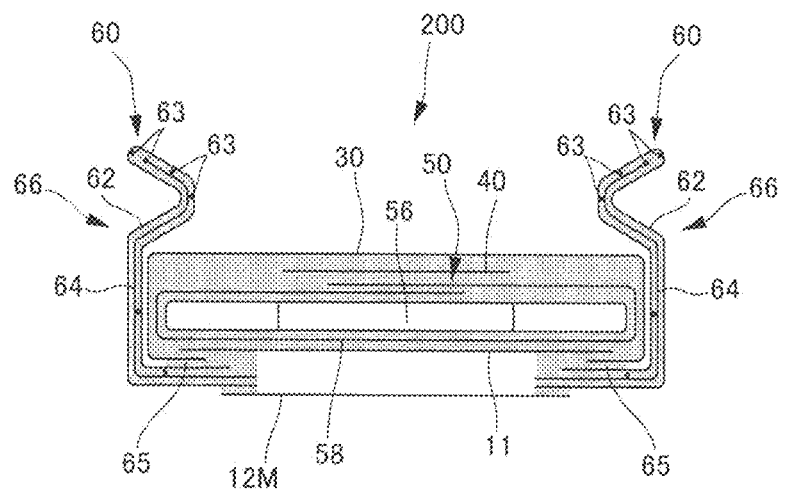
FIG. 3 is a cross-sectional view of FIG. 1 along line 3-3.
Figure 4:
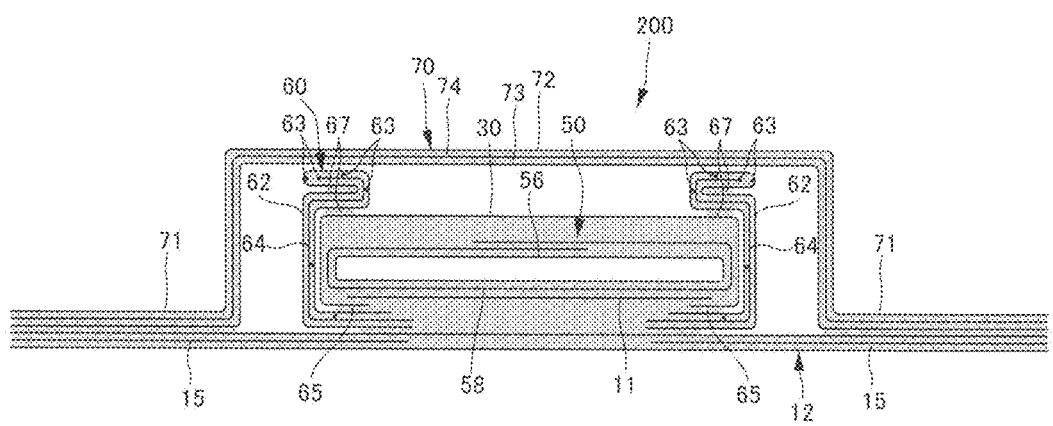
FIG. 4 is a cross-sectional view of FIG. 1 along line 4-4.
Figure 5:
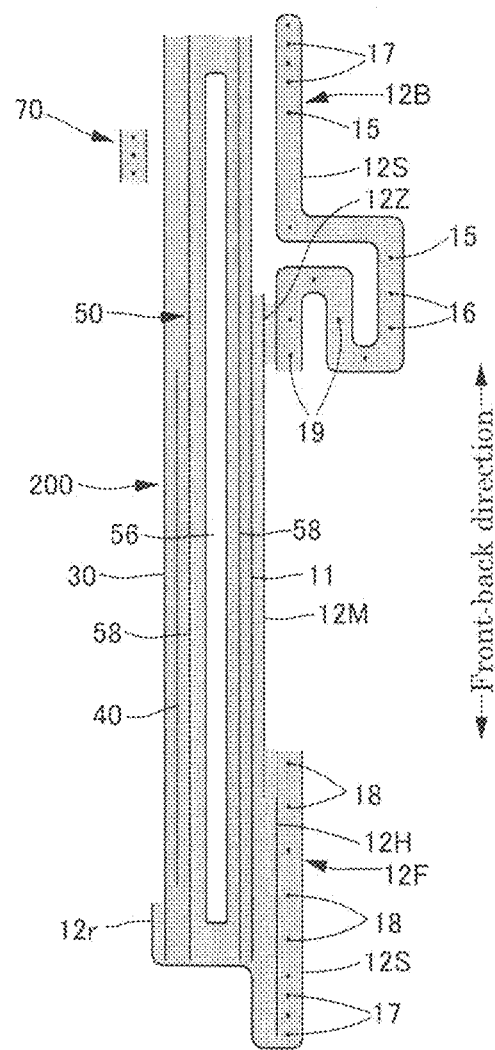
FIG. 5 is a cross-sectional view of FIG. 1 along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 3 to 5. Reference sign 40 indicates an interlayer sheet (second sheet) provided between the top sheet 30 and the absorbent element 50 to move quickly the liquid having passed through the top sheet 30 to the absorbent element 50 and to prevent reflowing. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.

(Interlayer Sheet)

To move the liquid having passed through the top sheet 30 quickly to the absorber, the interlayer sheet (also called as "second sheet") 40 higher in liquid permeation speed than the top sheet 30 may be provided. The interlayer sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet 40 may not be provided.

The interlayer sheet 40 may be made from the same material as that for the top sheet 30, or spun-laced, spun-bonded, SMS, or pulp non-woven fabric, or mixture sheet of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 g/m$^2$, more preferably 25 to 60 g/m$^2$. The fineness of raw fibers for the non-woven fabric is preferably 2.2 to 10 dtex. To increase the bulk of the non-woven fabric, all or some composite fibers of the raw fibers are preferably eccentric fibers with cores not centered, hollow fibers, or eccentric and hollow fibers.

The interlayer sheet 40 in the illustrated form is centered on an absorber 56 and is narrower than the absorber 56 in the width direction. Alternatively, the interlayer sheet 40 may be provided over the entire width of the absorber 56. The interlayer sheet 40 may be the same in length as the absorber 56, or may be shorter than the absorber 56, falling within the central area for receiving liquid.

(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction. Besides, the liquid impervious sheet 11 may be a non-woven fabric of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changing in color by absorption of liquid may be provided at the inside of the liquid impervious sheet 11, in particular, on the side surface of the absorber 56.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed such that a belt-like gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at a folded portion and its neighborhood. The base portions (ends opposite to the sheet folded portion in the width direction) of the three-dimensional gathers 60 positioned opposite to the forward edge portions constitute attachment portions 65 fixed to the under side surface of the inner body 200 at side edges. The portions of the three-dimensional gathers 60 other than the attachment portions 65 constitute protrusions 66 (folded portions) that protrude from the attachment portions 65. In addition, the protrusions 66 include the base portions toward the central side in the width direction and the edge portions that are folded back from the edges of the base portions toward the outside in the width direction. Although this form uses the three-dimensional gathers of surface-touching type, three-dimensional gathers (not illustrated) of a line-touching type that are not folded back toward the outside in the width direction may also be used. Then, while the both ends of the protrusions 66 in the front-back direction are front-back fixed portions 67 which are fixed to the side surfaces of the top sheet 30 in a lying down state with a hot-melt adhesive or a heat seal, the intermediate portions positioned therebetween are unfixed free portions to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m$^2$. The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 6:
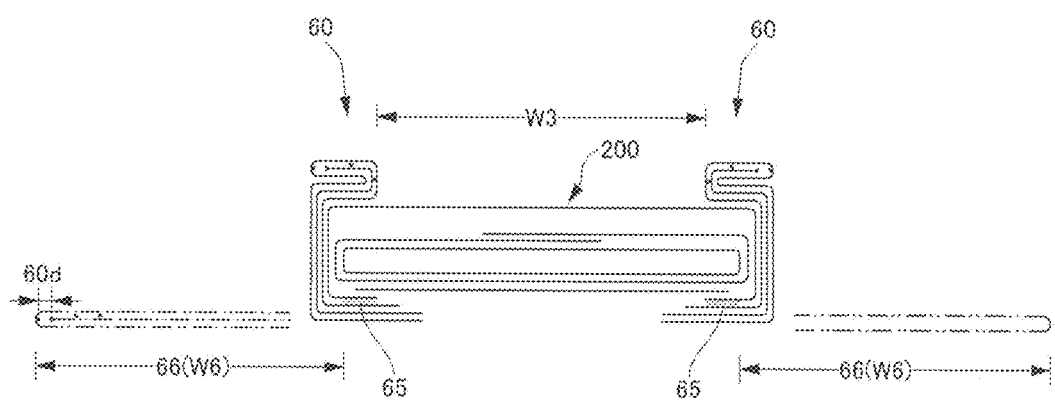
FIG. 6 is a cross-sectional view showing only major components of the underpants-type disposable diaper, together with dimensions.

The dimensions of the three-dimensional gathers 60 can be decided as appropriate. In the case of a disposable diaper for infants, however, the standing height W6 (width of the protrusions 66 in an open state) is preferably 15 to 60 mm, more specifically 20 to 40 mm as illustrated in FIG. 6, for example. In addition, the separation distance W3 between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

The absorber 56 may be rectangular in shape but preferably has an hourglass shape having a front end portion, a back end portion, and a narrower portion that is positioned between the front and back end portions and is narrower than the two end portions as illustrated in FIG. 1 to improve the absorber 56 and the three-dimensional gathers 60 in a fit of the edges around the legs.

The dimensions of the absorber 56 can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "powders" as well as "particles". The diameter of the high-absorbent polymer particles 54 may be the same as that of particles for general use in this type of absorbent article. For example, the ratio of particles that remain on a sieve after sieving (shaking for five minutes) with a standard sieve (JIS Z8801-1:2006) of 500 µm is preferably 30 weight % or less. Alternatively, the ratio of particles that remain on the sieve after sieving (shaking for five minutes) with the standard sieve (JIS Z8801-1:2006) of 180 µm is preferably 60 weight % or more.

There is no particular limitation on the material for the high-absorbent polymer particles but the material preferably has a water absorption capacity (JIS K7223-1996 "Testing method for water absorption capacity of super absorbent polymers") of 40 g/g or more. The high-absorbent polymer particles may be based on starch, cellulose, or synthetic polymer. The high-absorbent polymer particles may be made of a starch-acrylic acid (salt) graft copolymer, a saponified material of starch-acrylonitrile copolymer, a crosslinking substance of carboxymethyl-cellulose sodium, an acrylic acid (salt) polymer, or the like. The high-absorbent polymer particles are preferably used in a general particulate form but may be used in another form.

The water absorption rate (JIS K7224-1996 Testing method for water absorption rate of super absorbent polymers) of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The gel strength of the high-absorbent polymer particles is preferably 1000 Pa or more. Accordingly, it is possible to suppress effectively a sticky feeling of the absorber 56 after liquid absorption even when the absorber 56 is of high bulk.

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Crotch Portion Cover Sheet)

To the back surface of the liquid impervious sheet in the inner body 200 can be attached a crotch portion cover sheet 12M so as to cover a part of exposed portion of the inner body 200 (for example, along the entire front-back direction of the exposed portion between the ventral side outer body 12F and the dorsal side outer body 12B but not extending to the front and back ends of the inner body 200, or both side edges in the width direction not reaching the both side edges of the inner body 200) or the entire inner body 200. A material for the crotch portion cover sheet 12M similar to that of the outer bodies 12F and 12B may be used as explained below.

(Outer Body)

The outer bodies 12F and 12B have waist portions T having the side seal portions 12A and determined as vertical areas (vertical areas from the waist opening to the upper ends of the leg openings) and an intermediate portion L determined as a front-back area of a portion forming the leg openings (between a vertical region of the ventral-side outer body 12F having the side seal portions 12A and a vertical region of the back-side outer body 12B having the side seal portions 12A). The waist portions T are conceptually divided into "waist edge portions" W forming the edge of the waist opening and "lower waist portions" U as the portions under the waist edge portions W. The lengths of these portions in the vertical direction vary depending on the size of the product and can be decided as appropriate. As an example, the length of the waist edge portion W may be 15 to 40 mm, and the length of the lower waist portion U may be 65 to 120 mm. On the other hand, the intermediate portion L can be also omitted or the intermediate portions L can be provided on both of the ventral-side outer body and the back-side outer body. In the form illustrated in the drawings, however, the intermediate portion L is provided on only the back-side outer body 12B and covers buttocks. When the edges of the intermediate portion L at the leg sides are formed into curved shapes so as to be around the legs, the fit around the legs are excellent and it is therefore preferable.

The outer bodies 12F and 12B are constituted by the ventral-side outer body 12F and the back-side outer body 12B, and the ventral-side outer body 12F and the back-side outer body 12B are not continuous at the leg sides and are separated from each other. A separation distance L8 therebetween may be set to approximately 150 to 250 mm.

As illustrated in FIGS. 3 to 5, the outer body 12, 13 is formed by sticking an inner layer and an outer layer composed of sheet materials 12S and 12H that are to be the outer body 12 and 13, with an adhesive such as a hot-melt adhesive and the like. In the illustrated form, one sheet material 12S of the dorsal side outer body 12B is folded back at the waist side to form the inner layer and the outer layer. While the inner sheet material 12H located within the ventral side outer body 12F only extends to the edge of the waist opening, the outer sheet material 12S wraps around the waist side edge of the inner sheet material 12H and is folded back inside at the waist side edge. This folded part 12W is extended to cover the upper end portion of the waist side edges of the inner body 200. It is needless to say that the ventral side outer body 12F may be formed by folding back one sheet material 12S in the same manner as the dorsal side outer body 12B. To the contrary, the dorsal side outer body 12B may be formed by sticking the outer sheet material 12S and the inner sheet material 12H together in the same manner as the ventral side outer body 12F. and a sheet structure of the ventral side outer body 12F and that of the dorsal side outer body 12B may be reversed.

There is no specific limitation on the sheet materials 12S and 12H as far as they are sheet-like, but they are preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. When the non-woven fabric is used, it is preferable that the basis weight thereof is approximately 10 to 30 g/m$^2$.

Also as illustrated in FIGS. 2 and 5, in the ventral side outer body 12F and the dorsal side outer body 12B, elongated resilient and elastic members 15 to 19 such as rubber threads are provided at a predetermined extension ratio between the inner layer and the outer layer composed of the sheet materials 12S and 12H, in order to enhance the fit around the wearer's waist.

The elongated resilient and elastic members 15 to 19 may be made from a synthetic rubber or a natural rubber. To stick the two sheet materials 12S and 12H of the outer bodies 12F and 12B and fix the elongated resilient and elastic members 15 to 19 sandwiched between the sheet materials, a hot-melt adhesive can be used by various application methods, or heat sealing or ultrasonic adhesion can be used.

When the elongated resilient and elastic members 15 to 19 are used, same resilient and elastic members can be uniformly provided. It is preferable, however, to make fineness, spacing, or the like different depending on a position of the outer bodies 12F and 12B. Thus, in the illustrated form, a plurality of waist edge resilient and elastic members 17 is fixed at the waist edge portion W in the extended state along the width direction at a predetermined extension ratio with spacing therebetween in the up-down direction in such a manner as to be entirely continuous in the width direction. One or more of the waist edge resilient and elastic members 17 in a region adjacent to the lower waist portion U may overlap the inner body 200 or may be provided on a lateral side of a central portion in the width direction overlapping with the inner body 200 so as to be continuous in the width direction. As the waist edge resilient and elastic members 17, about 3 to 22 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 150 to 400%, in particular about 220 to 320%, with spacing of 4 to 12 mm. All of the waist edge resilient and elastic members 17 may not be equal in thickness and extension ratio. For example, the resilient and elastic members may be different in fineness and extension ratio between the upper and lower sides of the waist edge portions W.

In the lower waist portions U, a plurality of lower waist portion resilient and elastic members 15 and 18 composed of elongated resilient and elastic members is fixed in the extended state along the width direction at a predetermined extension ratio with up-down direction space therebetween in such a manner as to be entirely continuous in the width direction, at upper sides and at the lateral sides of central portions of the lower waist portions U in the width direction overlapping the inner body 200.

As the lower waist portion resilient and elastic members 15 and 18, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, with spacing of 1 to 15 mm, in particular 3 to 8 mm.

(Extensible Structure)

The dorsal side outer body 12B is characterized in that edges of the central portion in the width direction are joined with the inner body 200 on the crotch side to form an inner body joined section 12Z, a length in the front-back length of a side in the outer body closer to the waist than to the inner body joined section 12Z is extensible to the crotch side, and a portion of the inner body disposed closer to the waist than to the inner body joined section 12Z of the inner body 200 can be moved to the crotch side relative to the dorsal side outer body 12B.

There is no specific limitation on the structure (extensible structure of the outer body) in which the length in the front-back direction of the side in the outer body closer to the waist than to the inner body joined section 12Z is extensible to the crotch side. In the first form, however, as illustrated in FIG. 12(*a*), a part of the dorsal side outer body 12B disposed at the crotch side is folded in the front-back direction once or a few times in a zigzag manner, both lateral side end portions of the crotch side portion are fixed with hot-melt adhesive or the like in a folded state to constitute non-unfolded parts 12*k*, and a part between the non-unfolded parts 12*k*, 12*k* is unfixed and unfolded so that a folded part 12W is formed. The inner body 200 is joined to a portion of the folded part disposed closer to a forward edge than to a fold closest to the forward edge in the folded part 12W with the hot-melt adhesive or the like to form the inner body joined section 12Z. The folded part 12W is unfolded so that the length in the front-back length of the side in the outer body closer to the waist than to the inner body joined section 12Z is extensible to the crotch side. Further in the first embodiment, in the folded part 12W, the elongated oblique resilient and elastic members 19 are provided which are fixed in an extended state along the width direction and which are in an oblique direction when the diaper is worn while the folded part is folded over an entire width direction. The oblique resilient and elastic members 19 are provided in the lateral side of the central portion overlapping the inner body 200 in the width direction, and are along the width direction when the folded part 12W is in the non-unfolded state. Further in the illustrated form, in an upper side region of the intermediate portion L, in a lateral side of the central portion overlapping the inner body 200 in the width direction, a plurality of resilient and elastic members 16 composed of elongated resilient and elastic members which continue in the width direction is fixed in the extended state along the width direction at a predetermined extension ratio with spacing therebetween in the up-down direction.

Figure 7:
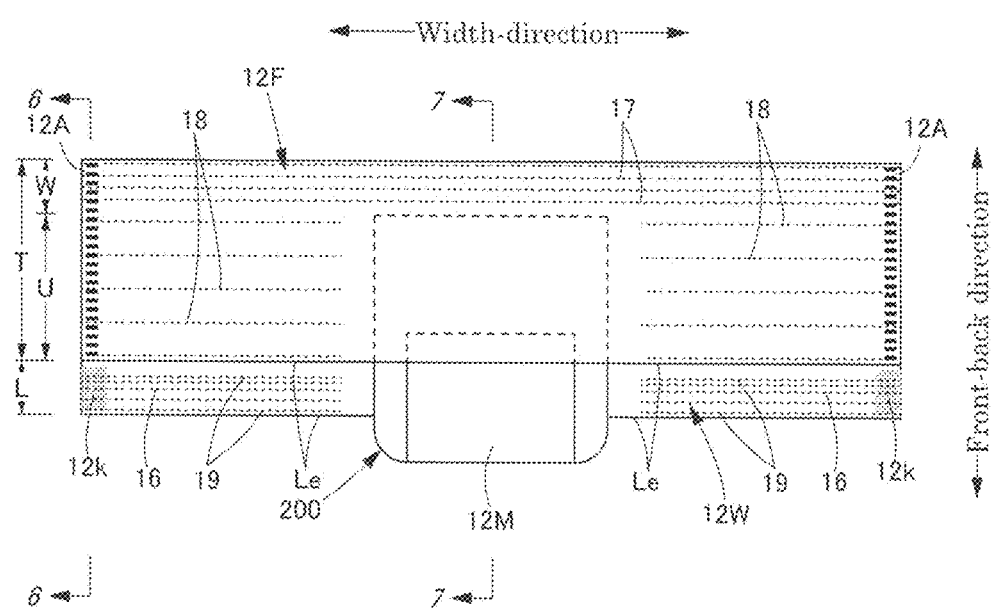
FIG. 7 is a front view of the underpants-type disposable diaper in the open state.
Figure 8:
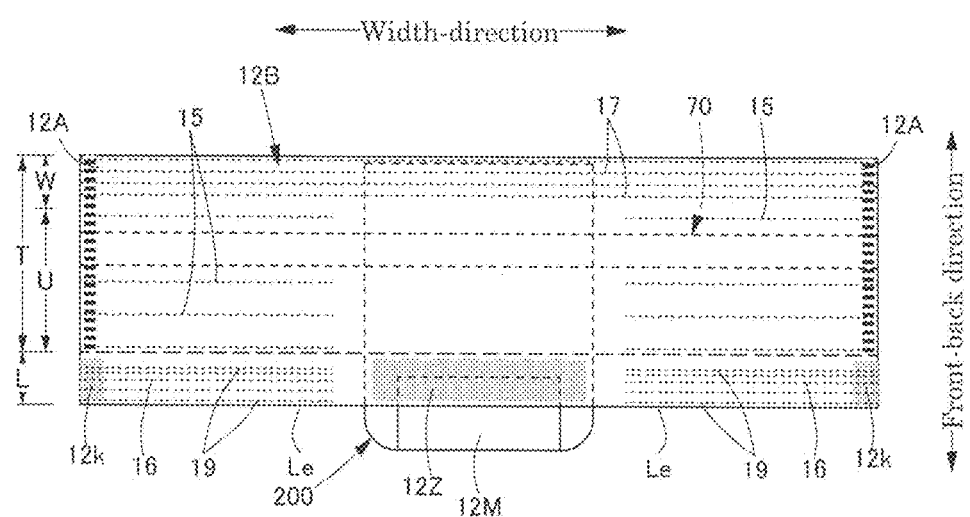
FIG. 8 is a rear view of the underpants-type disposable diaper in the open state.
Figure 9:
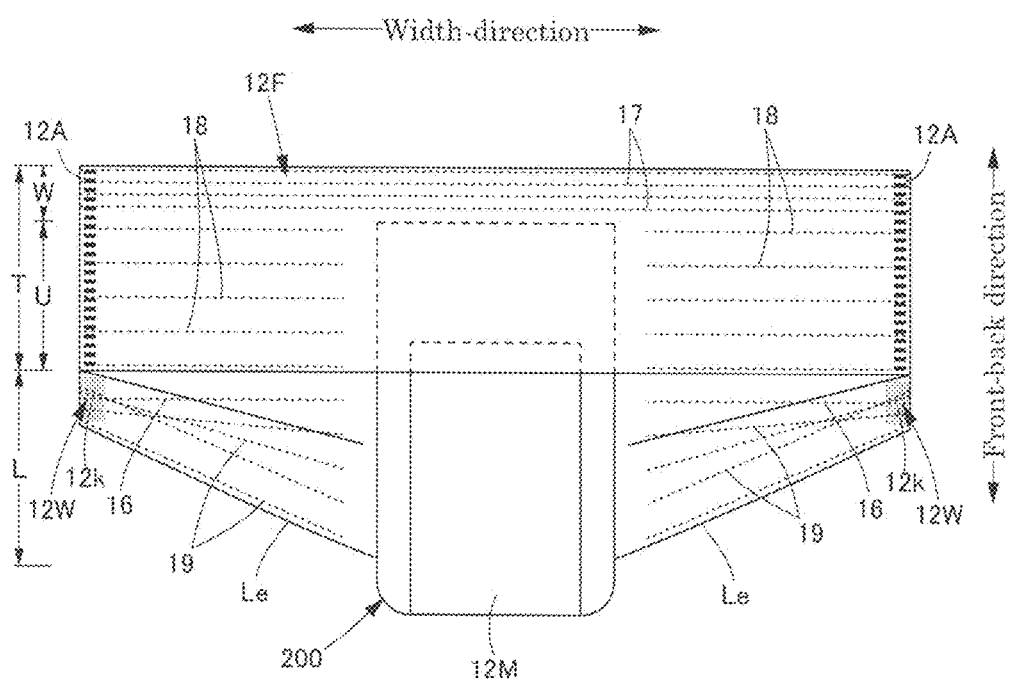
FIG. 9 is a front view of the underpants-type disposable diaper in the open state (extended state in the crotch side)
Figure 10:
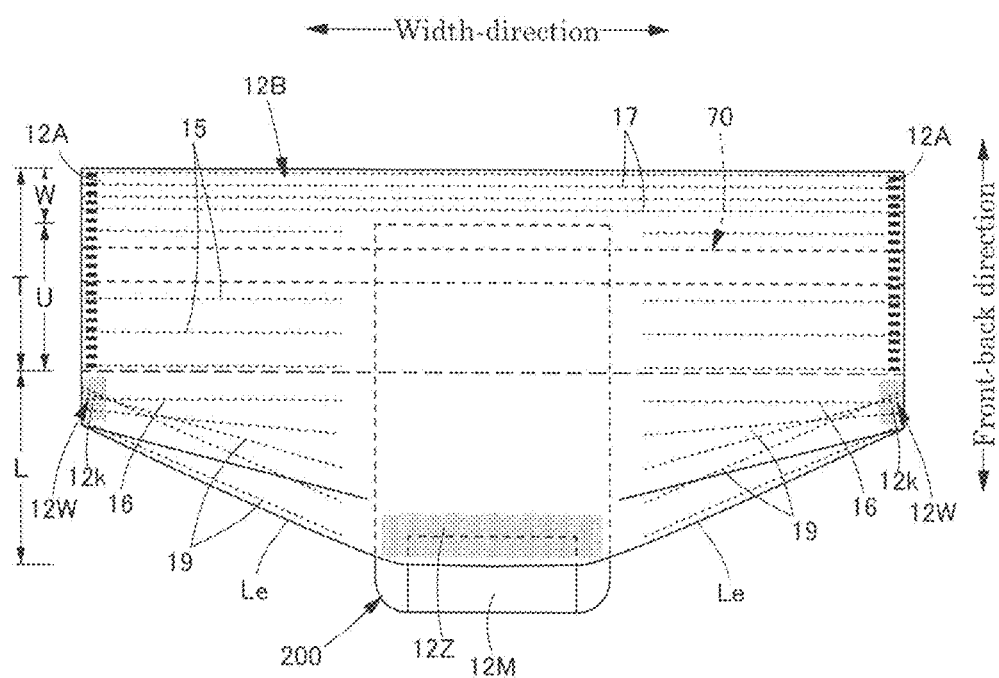
FIG. 10 is a rear view of the underpants-type disposable diaper in the open state (extended state in the crotch side)
Figure 11A:
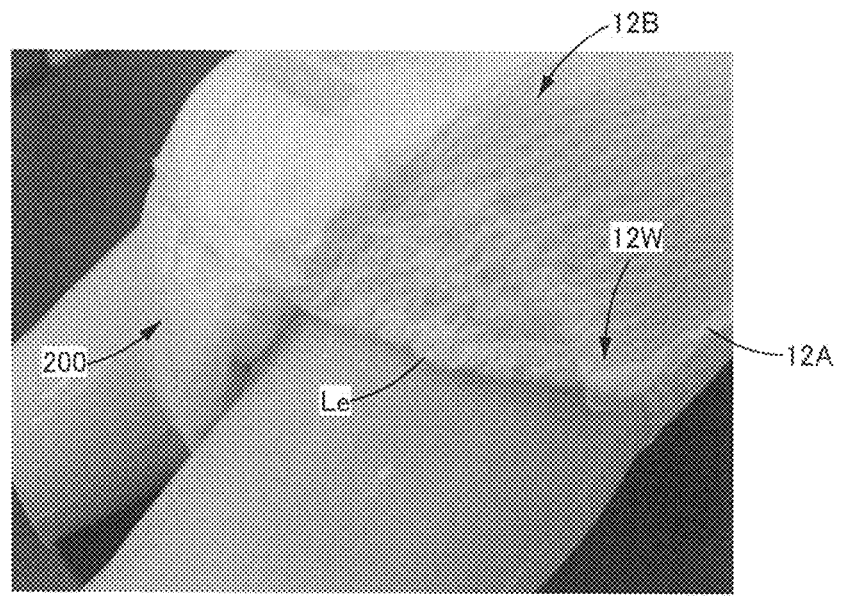
FIGS. 11(a) and (b) are photographs of samples of underpants-type disposable diapers.
Figure 11B:
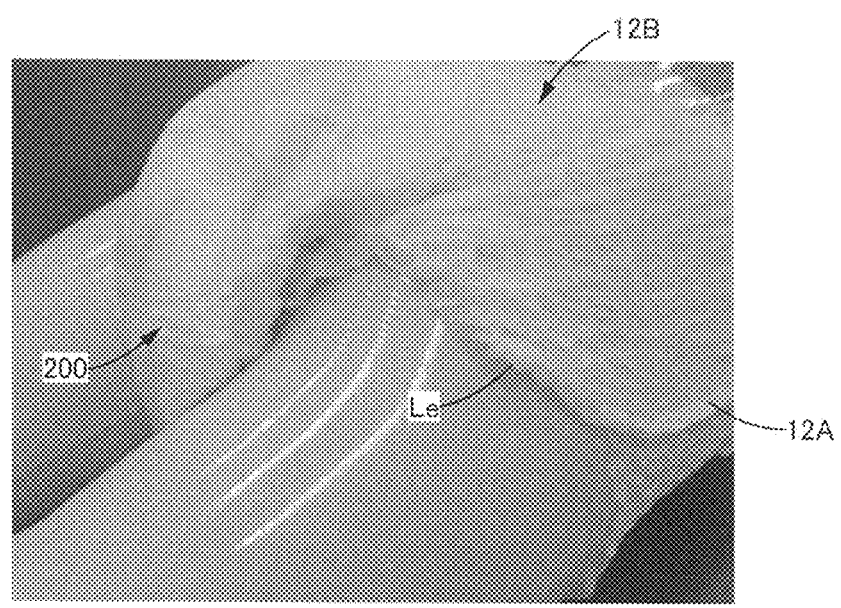
Figure 12A:
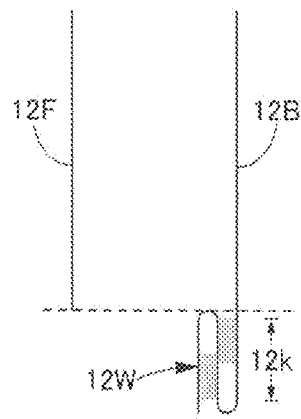
FIGS. 12(a) and (b) show schematic views of cross sections at a position of line 6-6 and a position of line 7-7 of FIG. 7 in various forms.
Figure 12B:
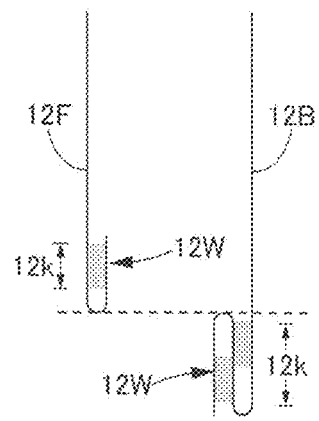
Figure 12B:
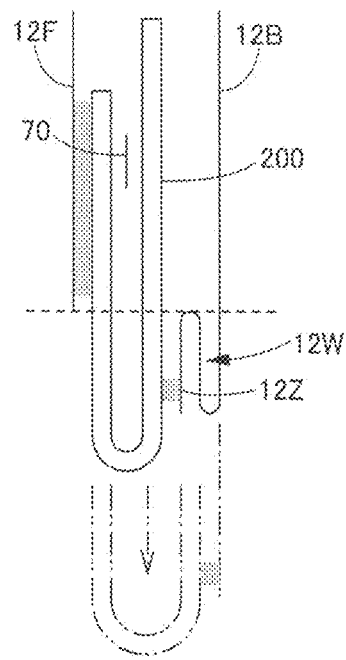
Figure 12B:
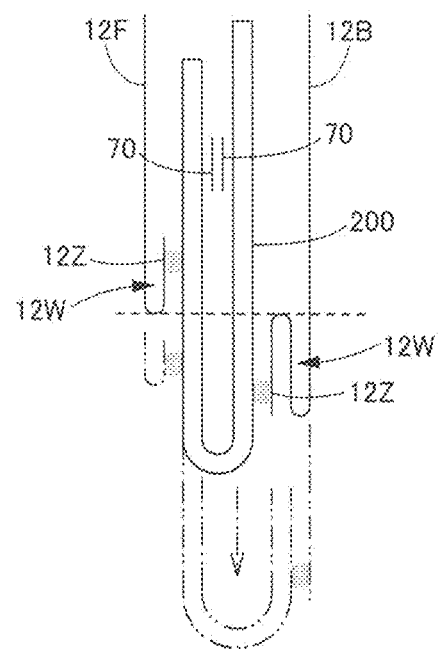

In this first form, from an unextended state illustrated in FIGS. 7 and 8, the length in the front-back direction of the side closer to the waist than to the inner body joined section 12Z in the dorsal side outer body 12B is extended to the crotch side, by unfolding the folded part 12W to the crotch side as it is closer to the center in the width direction, while the inner body 200 is moved to the crotch side relative to the dorsal side outer body 12B, as illustrated in FIGS. 9 and 10 and as illustrated by double-dot chain line in FIG. 12(*a*). Then, the edges Le of the leg openings positioned in the lateral side of the inner body 200 in the dorsal side outer body 12B obliquely face up to the side edge portions, and thus the edges Le of the leg openings are formed to fit around the wearer's buttocks. Such deformation can be made not only manually when the product is used, but also naturally when the diaper is pulled up to the waist and attached, or by force applied to the diaper (for example, when the resilient and elastic member is built-in to improve the fit, the contraction force thereof, or force of gravity applied to the inner body 200) after producing. Therefore, the diaper has an excellent fit of the edges around the legs at least in the worn state. In addition, in the first form, when the diaper is worn, the edges Le of the leg openings positioned to the lateral side of the inner body 200 in the dorsal side outer body 12B obliquely face up to the side edge portions, and the contraction force of the oblique resilient and elastic members 19 act along the edges. Thus, the edges Le of the leg openings closely fit well around the wearer's buttocks or the groin region. The oblique resilient and elastic members 19 may not be provided.

FIG. 9(*a*) is a photograph of a dummy doll wearing a sample item fixed to the dorsal side outer body 12B with the inner body 200 moved to the crotch side, in the form illustrated in FIGS. 1 to 8 and FIG. 12(*a*). FIG. 9(*b*) is a photograph of a dummy doll to which a commercially available product of an outer halved type having neither folded and unfolded structure nor oblique resilient and elastic members 19 is attached. As can be seen from a comparison of the photographs, in the sample according to the present invention, the edges Le of the leg openings of the dorsal side outer body 12B fit better to the buttocks and can cover the buttocks well.

The folded part 12W may be provided only on the dorsal side outer body 12B as illustrated in FIG. 12(*a*) as well as on both the ventral side outer body 12F and the dorsal side outer body 12B as illustrated in FIGS. 12(*b*), 13, and 14. In addition, the folded part 12W may be provided only on the ventral side outer body 12F although not illustrated.

Figure 13:
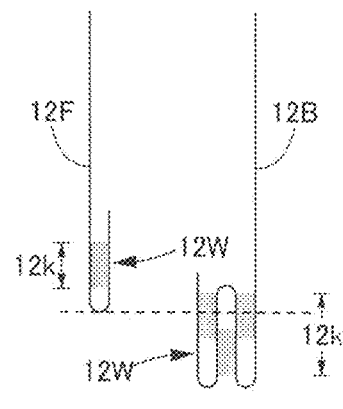
FIGS. 13(a) and (b) show schematic views of the cross sections at the position of line 6-6 and the position of line 7-7 of FIG. 7 in various forms.
Figure 13:
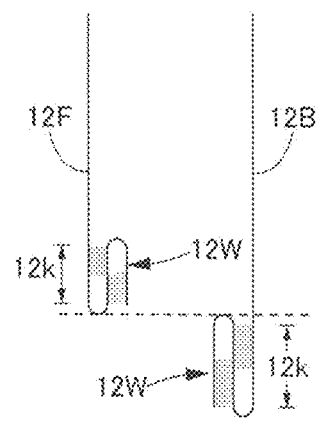
Figure 13:
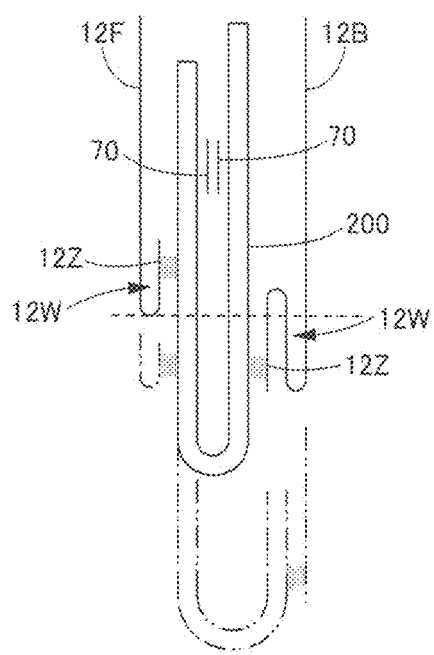
Figure 13:
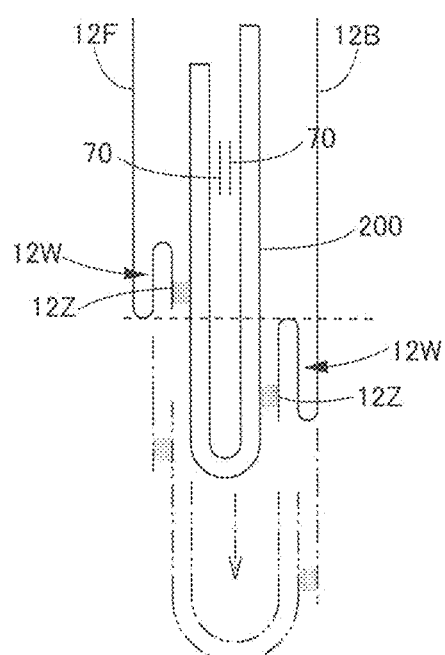
Figure 14:
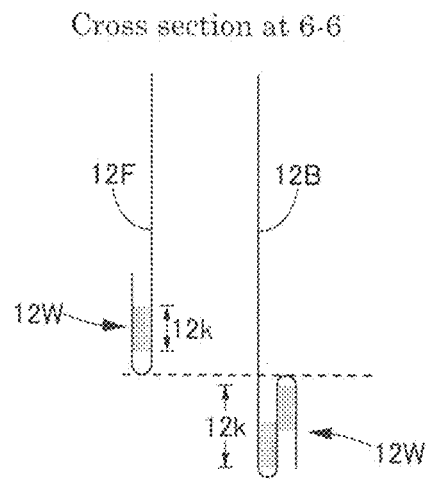
FIGS. 14(a) and (b) show schematic views of the cross sections at the position of line 6-6 and the position of line 7-7 of FIG. 7 in various forms.
Figure 14:
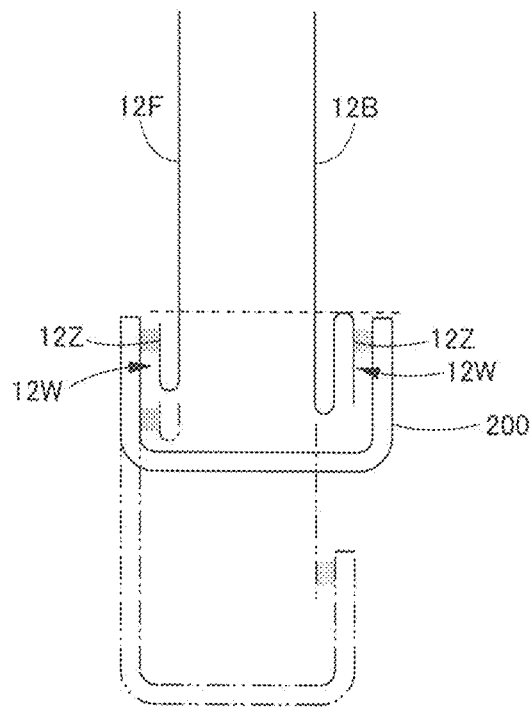
Figure 14:
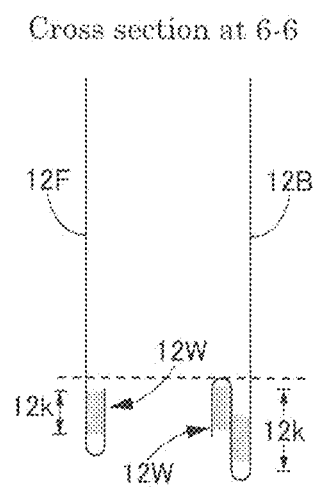
Figure 14:
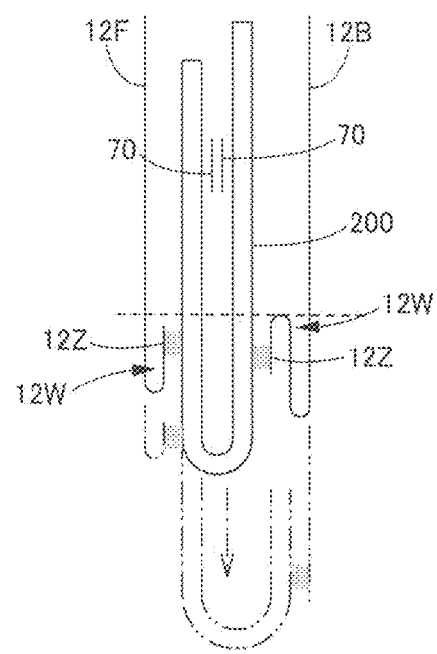
Figure 15:
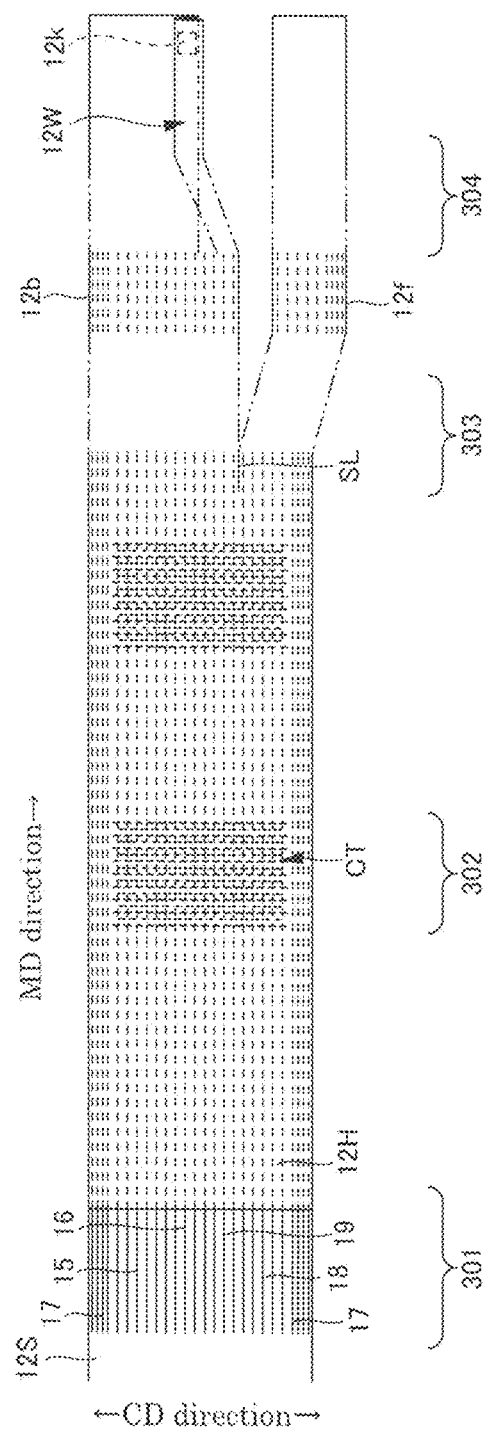
FIG. 15 is a planar view showing a producing flow of an underpants-type disposable diaper.

The folded part 12W may be folded in a direction toward the inside of the diaper as illustrated in FIGS. 12, 13, 14(*b*) as well as in a direction toward the outside of the diaper as illustrated in FIG. 14(*a*). When the folded part 12W is formed by folding inward as in the former case, the unfolded portion of the folded part 12W is unlikely to lift from the skin and fits tightly to the skin. In particular, when the folded part 12W is provided in the dorsal side outer body 12B, the unfolded portion of the folded part 12W is formed in a three-dimensional shape to cover the round buttocks. Meanwhile, when the folded part 12W is formed by folding outward as in the latter case, the unfolded portion of the folded part 12W fits softly to the skin by weak force.

The number of folds in the folded part 12W can be decided as appropriate, when the folded part 12W is provided in the dorsal side outer body 12B as illustrated in FIGS. 12, 13(*b*) to 14, forming an even number of folds widens the unfolded portion of the folded part 12W to cover the buttocks more widely. This effect is more significant in particular when the folded part 12W is folded in the direction toward the inside of the diaper.

In addition, as illustrated in FIGS. 12(*b*), 13(*a*), and 14, when the folded part 12W is provided in the ventral side outer body 12F, forming an odd number of folds allows the edges Le of the leg openings to enter into the valley of the human body while wrapping the round body part, thereby providing a favorable fit to the groin region. This effect is more significant in particular when the folded part 12W is folded in the direction toward the inside of the diaper.

The side seal portions 12A may be formed including the folded part 12W as illustrated in FIGS. 12(*b*) to 14(*a*). However, in the case of forming the side seal portions 12A by welding, when the number of overlaps in the sheet at the side seal portions 12A is locally large, the joining strength may vary resulting in risk of reducing productivity. Accordingly, the side seal portions 12A are preferably not formed in the leg opening side region having the folded part 12W as illustrated in FIGS. 12(*a*), 14(*b*), and 14. Accordingly, the side seal portions 12A can be stably joined to prevent reduction in productivity.

The dotted lines in FIGS. 12 to 14 represent the lower end of the side seal portions 12A. For example, in the dorsal side outer body 12B illustrated in FIG. 12(*a*), the waist portion T and the intermediate portion L are corresponding to the side edge correspondence region in the present invention, and the intermediate portion L is corresponding to the lower side portion (leg side portion) of the side edge correspondence region in the present invention, respectively. In the ventral side outer body 12F illustrated in FIG. 12(b), the waist portion T is corresponding to the side edge correspondence region in the present invention, and the lower side portion (leg side portion) of the waist portion T is corresponding to the lower side portion of the side edge correspondence region in the present invention, respectively. In the dorsal side outer body 12B illustrated in FIG. 13(a), the waist portion T and the intermediate portion L are corresponding to the side edge correspondence region, and the lower end portion of the waist portion T and the intermediate portion L are corresponding to the lower side portion of the side edge correspondence region, respectively. In addition, the dot patterns in FIGS. 12 to 14 represent the hot-melt adhesive.

On the other hand, according to the folded and unfolded structure of the present invention, as described above, the edges Le of the leg openings obliquely face up to the edge portions. Thus, the edges Le of the leg openings are not cut to fit around the wearer's legs, instead the edges can be formed around the wearer's legs even by configuring the ventral side outer body 12F and the dorsal side outer body 12B to be rectangular in shape in a state where the folded part 12W is unfolded. Yet in this case, as can be seen from a producing method described later, trim loss in the producing of the outer bodies 12F and 12B can be completely eliminated.

As the intermediate resilient ad elastic members 16 and the oblique resilient and elastic members 19, about 2 to 10 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 150 to 300%, in particular about 180 to 260%, with spacing of 5 to 40 mm, in particular 5 to 20 mm.

When the lower waist portion resilient and elastic members 15, 18 and the intermediate portion resilient and elastic members 16 and the oblique resilient and elastic members 19 are provided at the both sides of the central portions overlapping the inner body 200 in the width direction except for the central portions as illustrated in the drawings, the inner body 200 does not contract more than necessary in the width direction, thus the diaper does not become rough with deterioration in appearance and does not decrease in absorbing performance. The foregoing form includes the form in which the resilient and elastic members reside only at the both sides in the width direction, and the form in which the resilient and elastic members reside crossing over the inner body 200 from one side to the other side in the width direction, but the resilient and elastic members are finely cut and exert no contraction force at the central portion overlapping the inner body 200 in the width direction (this substantially means that no resilient and elastic members are provided), and thus the contraction force of the resilient and elastic members acts only at the both sides in the width direction. As a matter of course, the arrangement forms of the lower waist portion resilient and elastic members 15, 18 and the intermediate portion resilient and elastic members 16 and the oblique resilient and elastic members 19 are not limited to the foregoing examples. Alternatively, some or all of the lower waist portion resilient and elastic members 15, 18 and the intermediate portion resilient and elastic members 16 and the oblique resilient and elastic members 19 may be provided crossing over the inner body 200 from the one side to the other side in the width direction so that the stretching force acts on the entire lower waist portions U in the width direction.

In order to form a moving portion in the inner body 200 at a portion closer to the waist than to inner body joined section 12Z of the inner body 200, in the first form, as illustrated in FIG. 5, an entire portion closer to the waist than to the inner body joined section 12Z in the inner body 200 is not fixed to any other members including the dorsal side outer body 12B. Thus, as the illustrated form, when the inner body 200 extends to the side of the waist edge portion W, the portion closer to the waist than to the inner body joined section 12Z in the inner body 200 may move unnecessarily or excessively, resulting in a risk of deteriorated wearing feeling and leakage. Hence, in the first form, as illustrated in FIGS. 1 and 4, there is provided a pressing belt 70 that extends over the inner body 200 in the width direction in the side closer to the waist than to the inner body joined section 12Z in the dorsal side outer body 12B, the portion positioned at both sides of the moving portion of the inner body 200 in the width direction being fixed to the dorsal side outer body 12B with a hot-melt adhesive or the like, and the portion passing over the moving portion of the inner body 200 being not fixed. Reference sign 71 indicates the portion of the pressing belt 70 fixed to the dorsal side outer body 12B. With such a pressing belt 70 provided, the moving portion of the inner body 200 can be held down so as not to move unnecessarily or excessively, thereby enabling prevention of unintentional deformation such as bend and turn-up of the moving portion.

The pressing belt 70 may be formed of a material such as unstretchable sheet composed of non-woven fabric and the like. However, if it is stretchable in the width direction, the pressing belt can be held down not to move or roll up in the width direction, while allowing the moving portion of the inner body 200 to move in the front-back direction. Thus, while the pressing belt 70 of the illustrated form is made by sticking two sheet materials 72 and 73 composed of non-woven fabric or the like (they may be two-layer structured by being folded double or in C form) together, and fixing elongated resilient and elastic members 74 between the layers in the extended state along the width direction, a pressing belt of a material that can resiliently stretch, such as a rubber sheet and stretchable non-woven fabric, may also be used.

As illustrated in FIG. 12 or the like, if a structure is such that both the ventral side outer sheet and the dorsal side outer sheet are extensible to the crotch side, the pressing belt 70 may be provided both on the ventral side outer sheet and the dorsal side outer sheet.

<Example of a Method of Producing the First Form>

Figure 16:
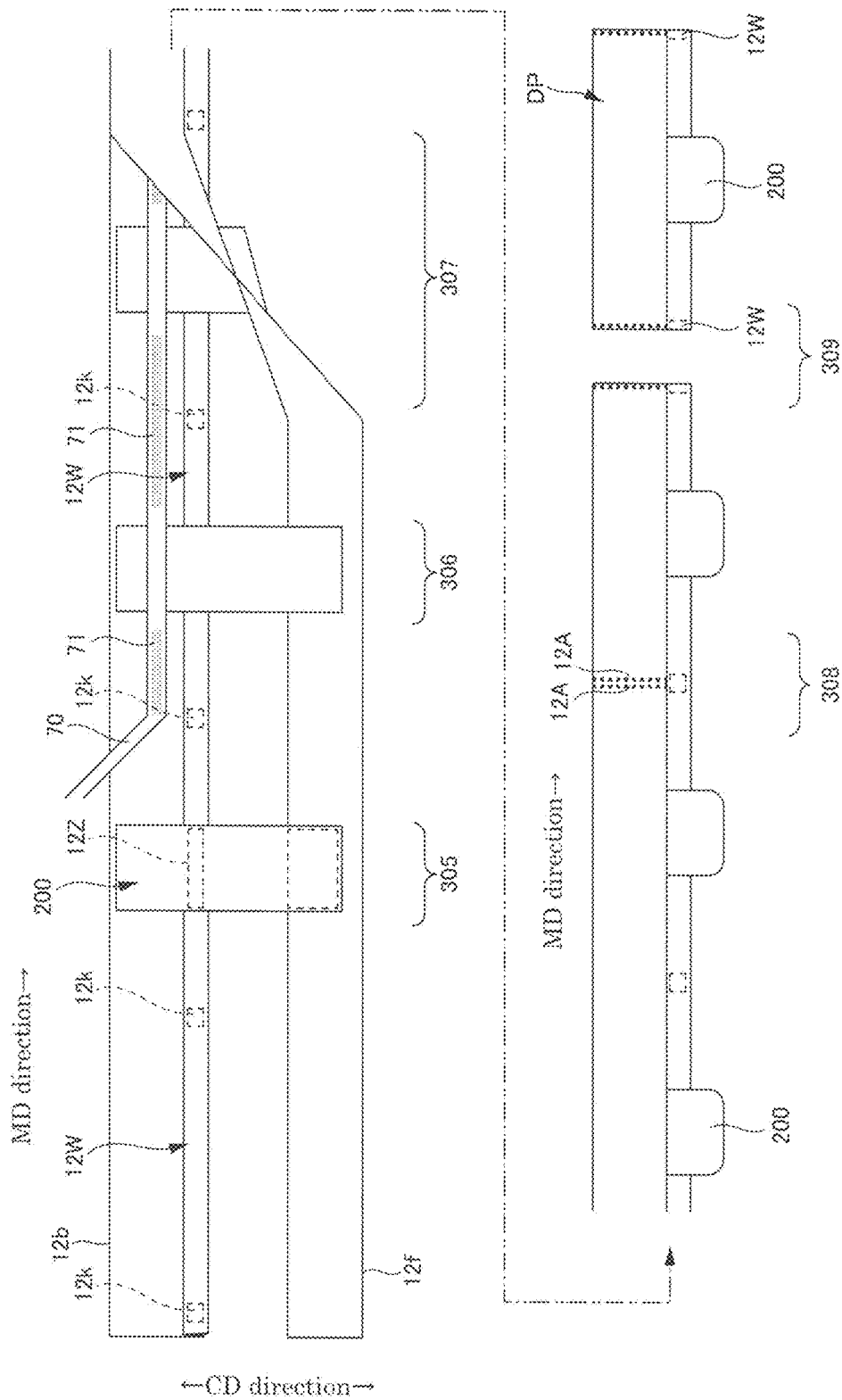
FIG. 16 is a planar view showing the producing flow of the underpants-type disposable diaper.
Figure 17:
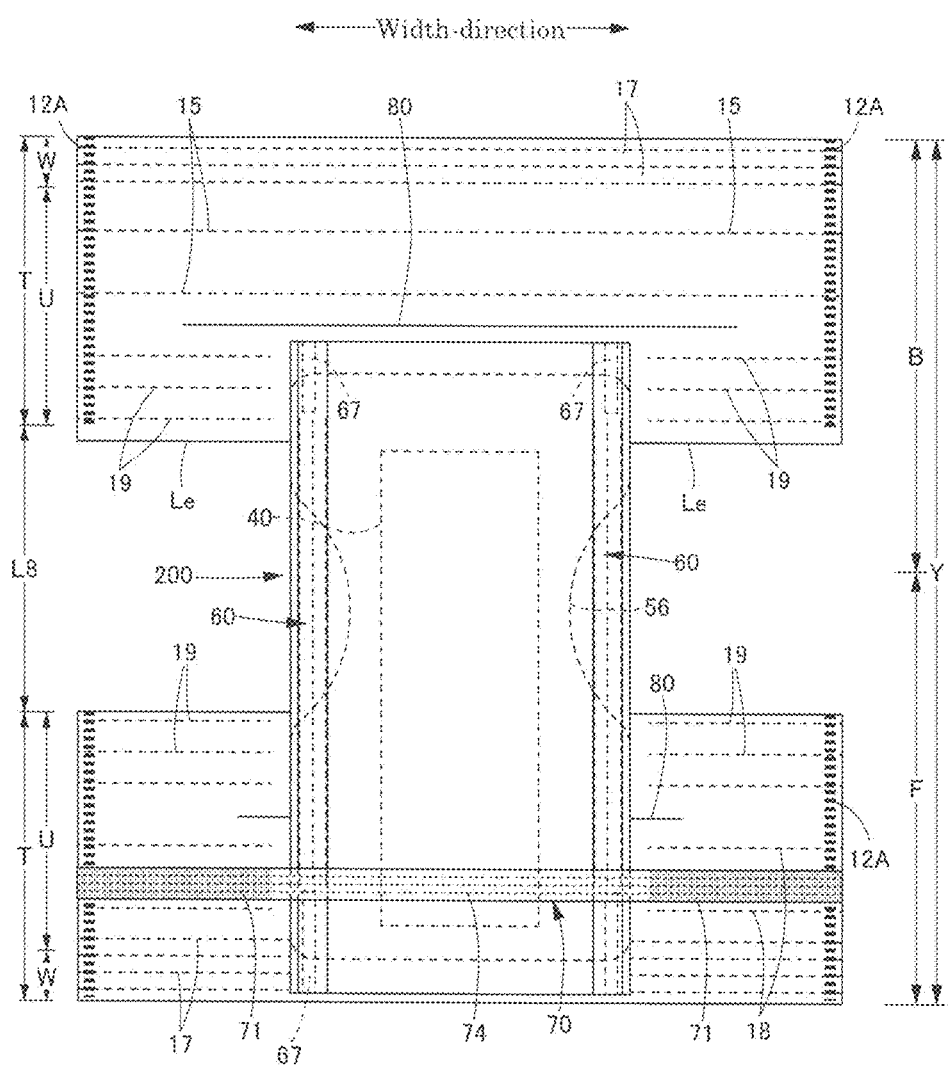
FIG. 17 is a planar view of an inner surface of an underpants-type disposable diaper in the open state.
Figure 18:
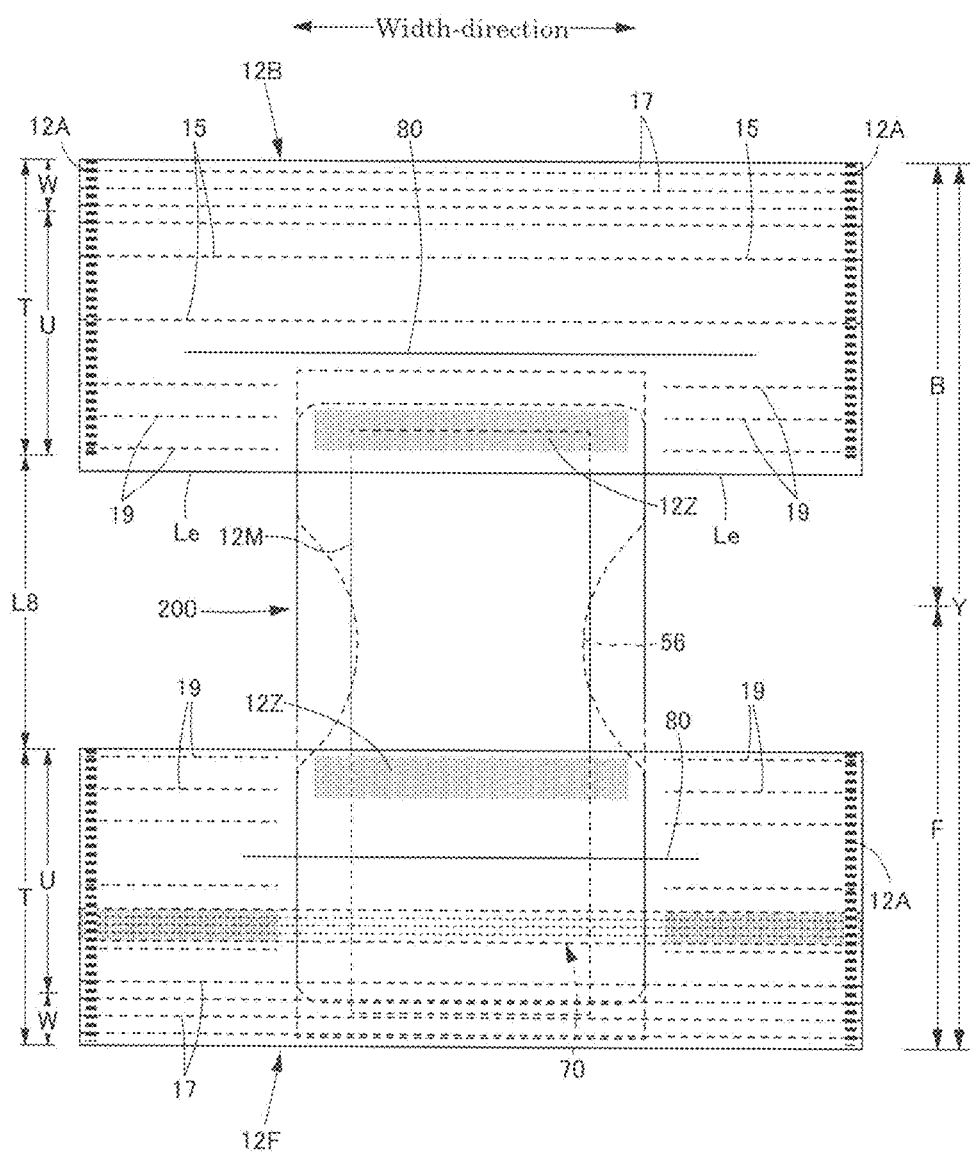
FIG. 18 is a planar view of an outer surface of the underpants-type disposable diaper in the open state.
Figure 19:
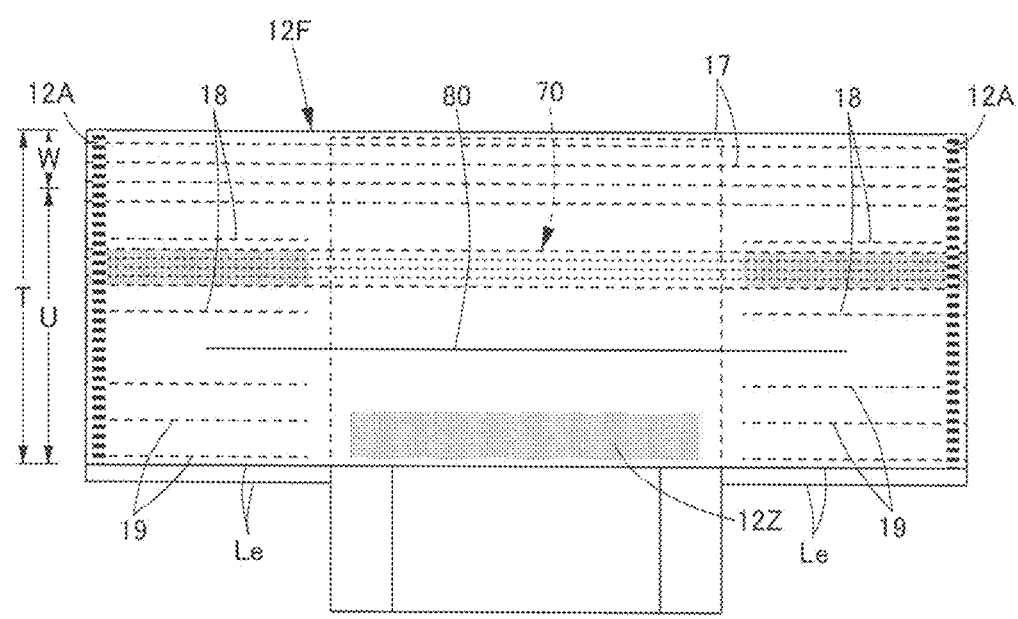
FIG. 19 is a front view of the underpants-type disposable diaper in the open state.

FIGS. 16 and 17 illustrate an example of a method for producing an underpants-type disposable diaper of the first form. This production line is formed for a lateral flow with the diaper width direction in parallel to the MD direction (machine direction or line flow direction). In this line, a ventral side elastic belt 12f that is to be a ventral side outer body 12F and a dorsal side elastic belt 12b that is to be a dorsal side outer body 12B are formed, and an inner body 200 produced in another line is attached to the ventral side elastic belt 12f and the dorsal side elastic belt 12b. For the sake of ease of understanding, the continuous members in the production process are given the same reference signs as those of the members after the production.

More specifically, the production line has a resilient member attachment step 301, a resilient member cutting step 302, a center slit step 303, a folding step 304, an inner body attachment step 305, a pressing belt attachment step 306, a folding up step 307, a side part joining step 308, and a cutoff step 309. Among these steps, the folding step 304 is more characteristic than the conventional production method.

Specifically, in the resilient member attachment step 301, while a belt-like sheet material 12H of predetermined width is conveyed in the continuous direction thereof, the elongated resilient members 15 to 19 such as rubber threads are fixed in an extended state in the MD direction, with spacing in the almost entire CD direction of the sheet material 12H. Furthermore, a belt-like material 12S of predetermined width is supplied along the continuous direction thereof to top surfaces of the elongated elastic members and stuck thereto to form an elastic belt. In the illustrated example a form is assumed in which two sheet materials 12S and 12H are stuck to sandwich the resilient and elastic members 15 to 19. However, the resilient and elastic members may also be sandwiched by folding one sheet material double or in C form.

Then, the resilient member cutting step 302 is carried out on the formed elastic belt, as needed. With predetermined spacing in the MD direction, the resilient and elastic members 15, 16, 18, and 19 positioned at a portion CT that will later overlap the inner body 200 are cut by a cutting device such as heat embossing so that the stretching force of the resilient and elastic members 15, 16, 18, and 19 do not act on the portion CT.

Then, in the outer bodies 12F and 12B cutting and splitting step 303, an intermediate predetermined region SL of the elastic member in the CD direction is cut along the MD direction to split the member into the ventral side elastic belt 12f and the dorsal side elastic belt 12b and expand spacing between the ventral side elastic belt 12f and the dorsal side elastic belt 12b to a predetermined distance. After the slitting, although a side edge (that is to be an edge Le of a leg opening) at the center side in the CD direction of at least one of the ventral side elastic belt 12f and the dorsal side elastic belt 12b may be cut off in a curved manner, as needed, such cutting is not carried out if trim loss is completely eliminated. Nevertheless, as described later, the edge Le of the leg opening may be formed so as to be along an oblique direction. In addition, in the illustrated example, the ventral side elastic belt 12f and the dorsal side elastic belt 12b are split separately in the cutting and splitting step 303 after being formed as an integrated elastic belt. However, by using different sheet materials to form the ventral side elastic belt 12f and the dorsal side elastic belt 12b, it is possible to omit the cutting and splitting step 304, and in doing so, the resilient and elastic members may be sandwiched by sticking two sheet materials as well as by folding one sheet material double or in C form.

Then, at the folding step 304, while the ventral side elastic belt 12f and the dorsal side elastic belt 12b are conveyed in parallel with a space therebetween in a CD direction, the edge side portion of the dorsal side elastic belt 12b on the ventral side elastic belt 12f side is folded once or plural times in a zigzag manner in the CD direction and fixed to form the folded part 12W. The fixed portion 12k of the folded part 12W can be formed by an appropriate joining means such as a hot-melt adhesive or heat sealing. Although not illustrated, in the case of providing the folded part 12W of the present invention on the ventral side as well, the edge side portion of the ventral side elastic belt 12f on the dorsal side elastic belt 12b side is also folded once or plural times in a zigzag manner in the CD direction to form the folded part.

Subsequently, in the inner body attachment step 305, the inner body 200 that is produced in advance in another line is supplied to the MD direction at predetermined spacing to form an inner assembled body by joining the front side portion of the inner body 200 to the ventral side elastic belt 12f and joining the back side portion of the inner body 200 only to the edge portion of the dorsal side elastic belt 12b on the ventral side elastic belt side. The joining and fixing can be performed with appropriate means such as a hot-melt adhesive, a heat seal, and the like.

Then, in the pressing belt attachment step 306, a continuous belt-like pressing belt 70 that is separately formed is supplied to traverse the inner body 200 along the MD direction, being fixed to the dorsal side outer body 12B intermittently at a region between the inner bodies 200 in the MD direction. This fixed portion 71 can be formed with appropriate means such as a hot-melt adhesive, a heat seal, and the like. The pressing belt attachment step 306 may not be provided.

Then, in the folding up step 307, after the inner assembled body is folded up at center in the CD direction so that an attachment surface of the inner body 200 of the ventral side elastic belt 12f overlaps an attachment surface of the inner body 200 of the dorsal side elastic belt 12b, in the side part joining step 308, the ventral side elastic belt 12f and the dorsal side elastic belt 12b are joined at portions that are to be both side portions of an individual diaper to form side seal portions 12A. In the cutoff step 309, the ventral side elastic belt 12f and the dorsal-side elastic belt 12b are cut at a boundary of individual diapers and individual diapers DP are obtained. The side part joining step 308 and the cutoff step 309 can be performed simultaneously.

According to such a producing method, a disposable diaper DP similar to the first form described above can be produced without the extension step of the dorsal side outer body 12B. Alternatively, oblique resilient and elastic members 19 that are in the oblique direction at least in the worn state even if an oscillation device is not used can be provided. Yet, cutting of leg openings is not needed and trim loss in the producing of the outer bodies 12F and 12B is completely eliminated.

<Second Form of the Underpants-Type Disposable Diaper>

Figure 20:
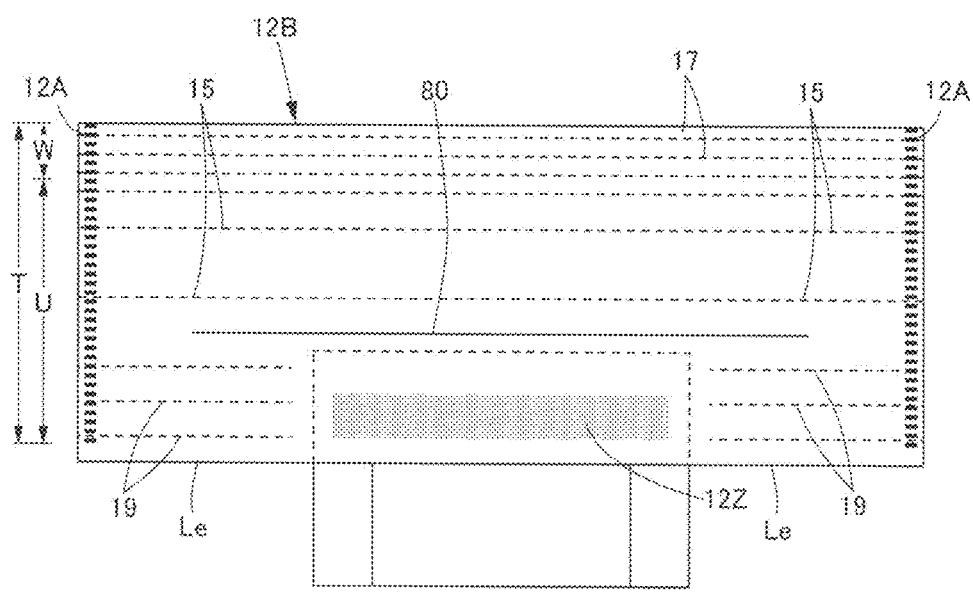
FIG. 20 is a rear view of the underpants-type disposable diaper in the open state.
Figure 21:
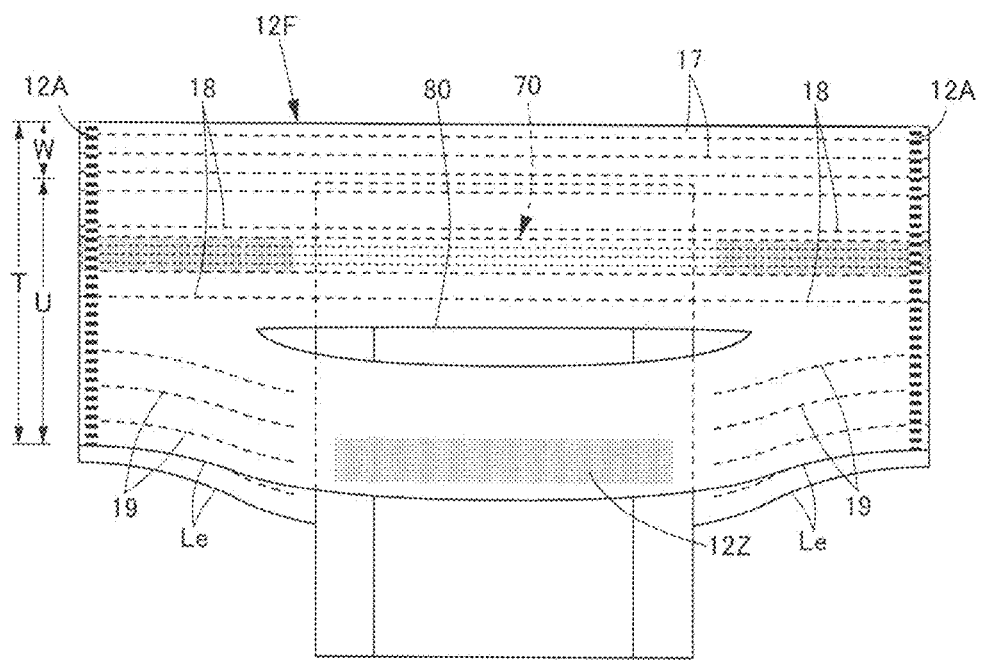
FIG. 21 is a front view of the underpants-type disposable diaper in the open state (extended state in the crotch side)
Figure 22:
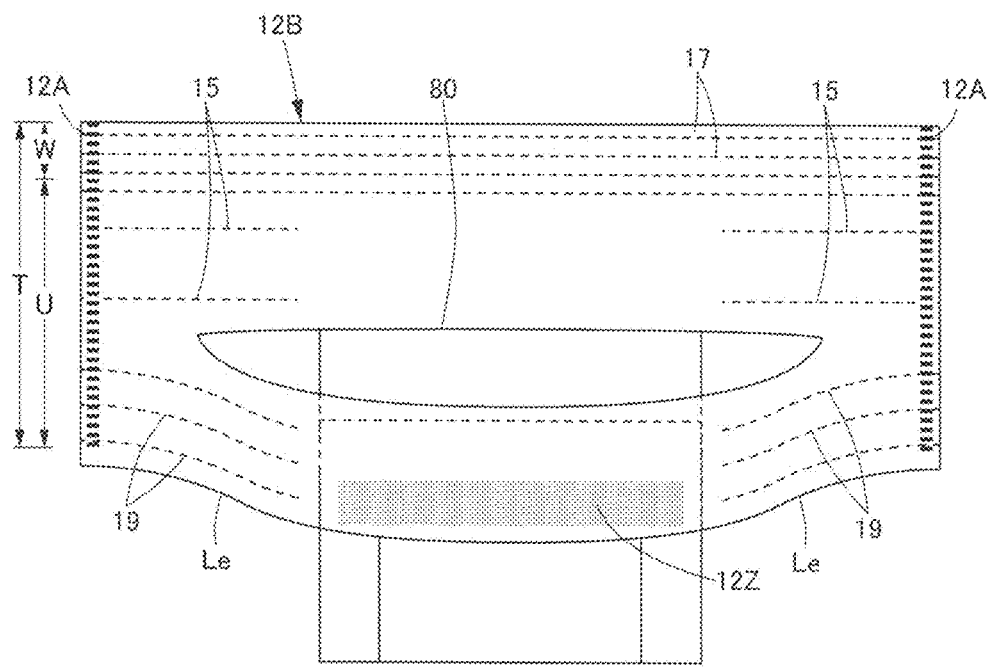
FIG. 22 is a rear view of the underpants-type disposable diaper in the open state (extended state in the crotch side)

A second form applies the extensible structure described in Patent Document 3, instead of the extensible structure with the folded part 12W in the first form. More specifically, as illustrated in FIGS. 18 to 22, separation portions 80 composed of a slit or an elongated opening extending in the width direction from one side to the other side at the center of the width direction are provided in the side closer to the waist side than the inner body joined sections 12Z in the ventral side outer body 12F and the dorsal side outer body 12B. By a change of shape from the state illustrated in FIG. 19 to separate the portion closer to the crotch side than the separation portion 80 to the crotch side with the respect to the portion at the waist side, as illustrated in FIG. 20, the front-back length at the side closer to the waist side than the inner body joined section 12Z is made extensible to the crotch side. In addition, on the separation portion 80 at the crotch side, elongated oblique resilient and elastic members 19 are provided that are fixed in the extended state along the width direction and that are in the oblique direction when the diaper is worn. While the separation portion 80 is preferably wider than the width of the inner body 200, the separation portion 80 may be narrow.

If the extensible structure of the outer bodies 12F and 12B is configured with such separation portions 80, edges Le of leg openings positioned in the lateral side of the inner body 200 in the outer bodies 12F and 12B obliquely face up to the side edge portions when the diaper is worn, and the contraction force of the oblique resilient and elastic members 19 act along the edges thereof. Thus, the edges Le of the leg openings closely fit well around the wearer's buttocks or the groin region. In addition, a very simple structure through only provision of a slit or the like does not increase the material cost and is easy to produce.

The second form is basically similar to that described in Patent Document 3, except that the portion closer to the waist side than to the inner body joined sections 12Z of the inner body 200 can be moved to the crotch side. Since details such as dimensions, shape, variants, and the like of the separation portion 80 are similar to the separation portions described in Patent Document 3, a description thereof is intentionally omitted. In addition, in the second form, a structure for prevention of inner body movement of a fourth form to be described below is adopted, and length of the inner body 200 is shorter. Also in the third form, however, the length of the inner body 200 can be made similar to that of the first form.

<Method of Producing the Second Form>

Figure 23:
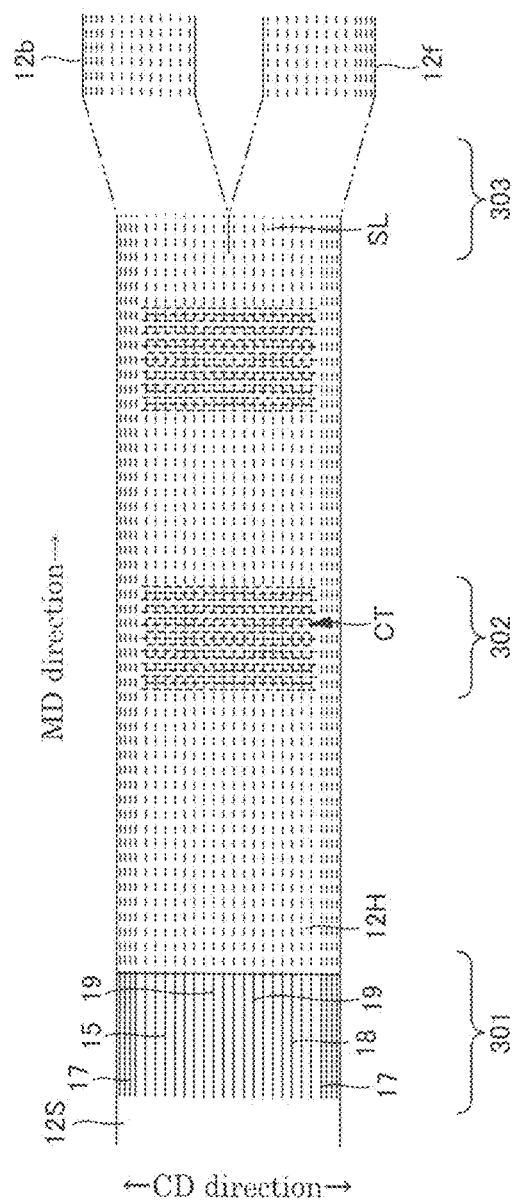
FIG. 23 is a planar view showing a producing flow of an underpants-type disposable diaper.
Figure 24:
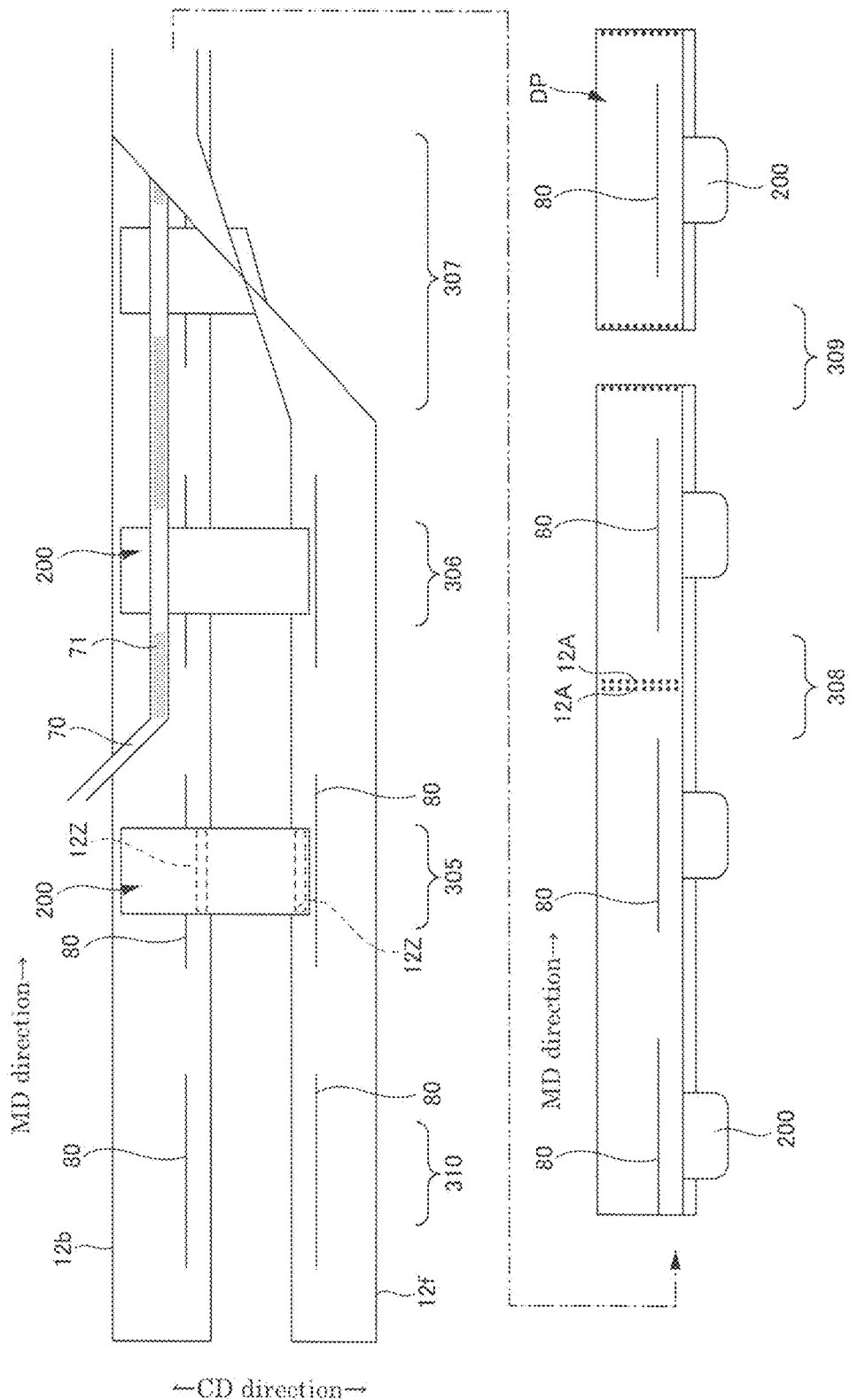
FIG. 24 is a planar view showing the producing flow of the underpants-type disposable diaper.
Figure 25:
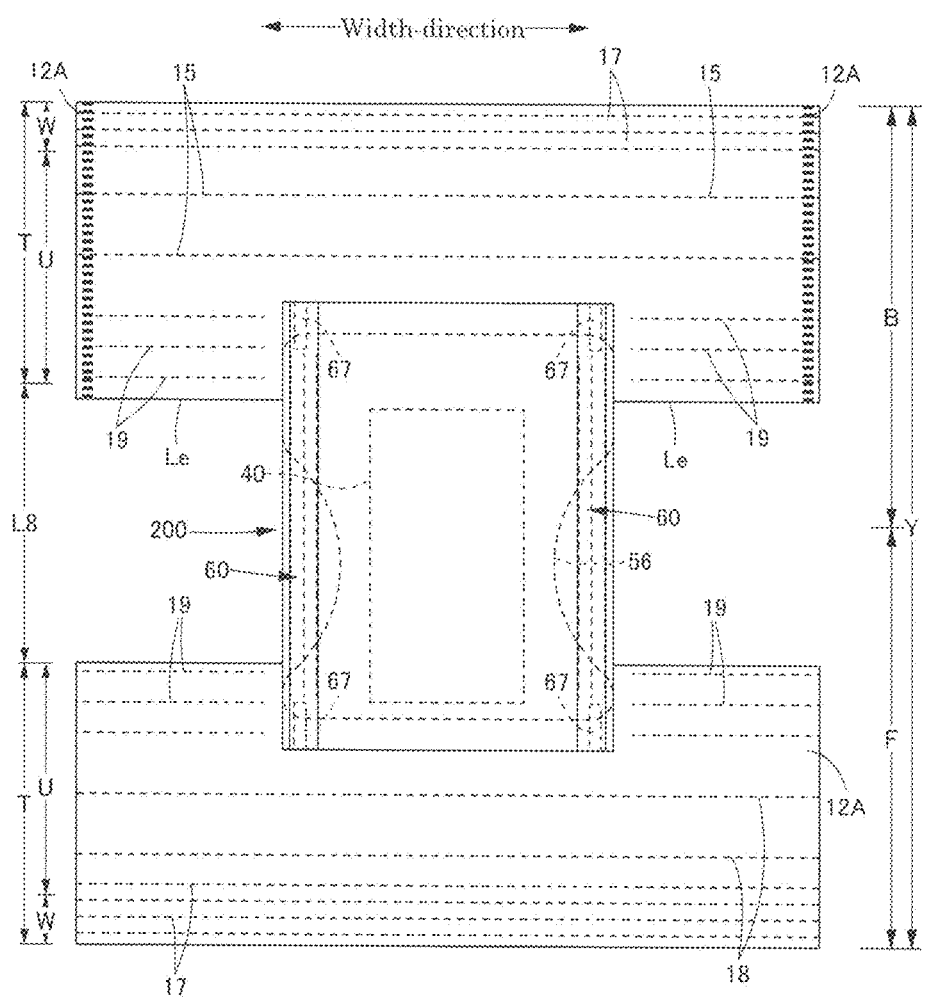
FIG. 25 is a planar view of an inner surface of an underpants-type disposable diaper in the open state.
Figure 26:
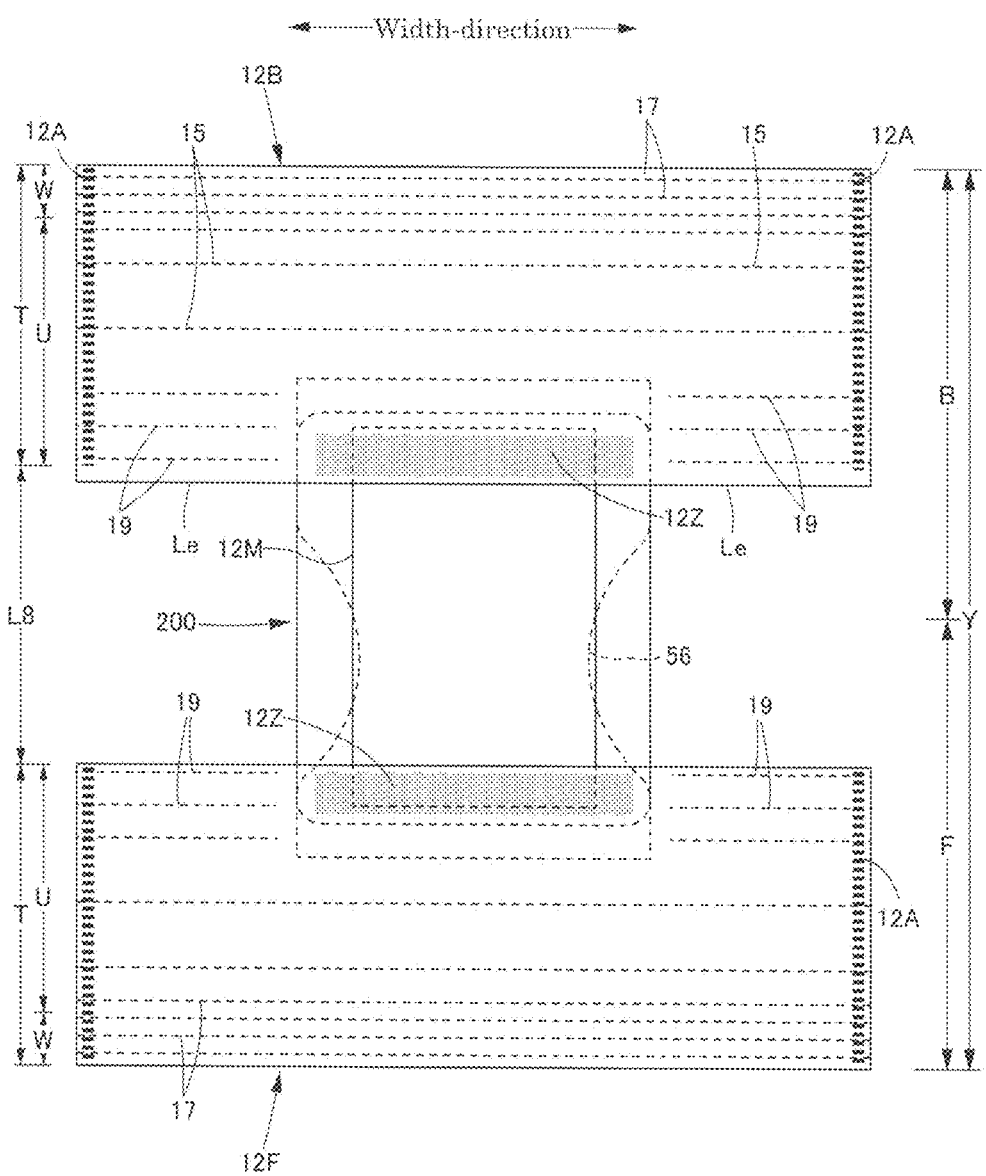
FIG. 26 is a planar view of an outer surface of the underpants-type disposable diaper in the open state.
Figure 27:
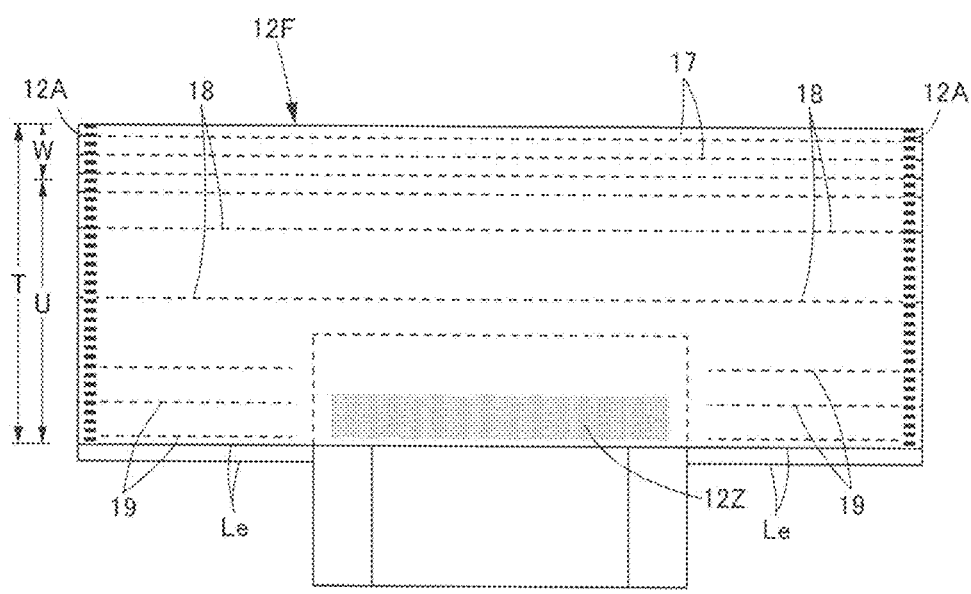
FIG. 27 is a front view of the underpants-type disposable diaper in the open state.
Figure 28:
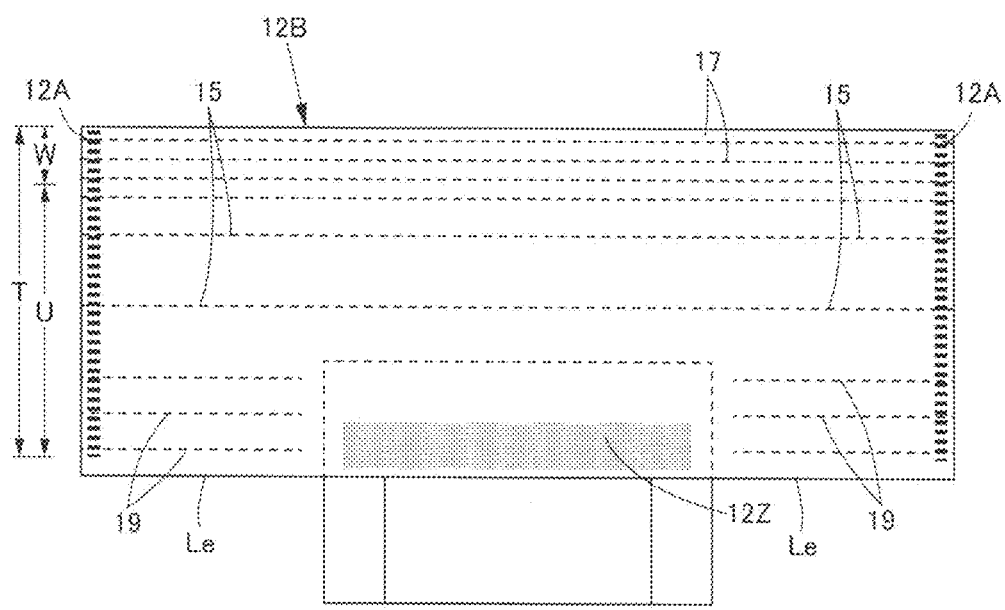
FIG. 28 is a rear view of the underpants-type disposable diaper in the open state.
Figure 29:
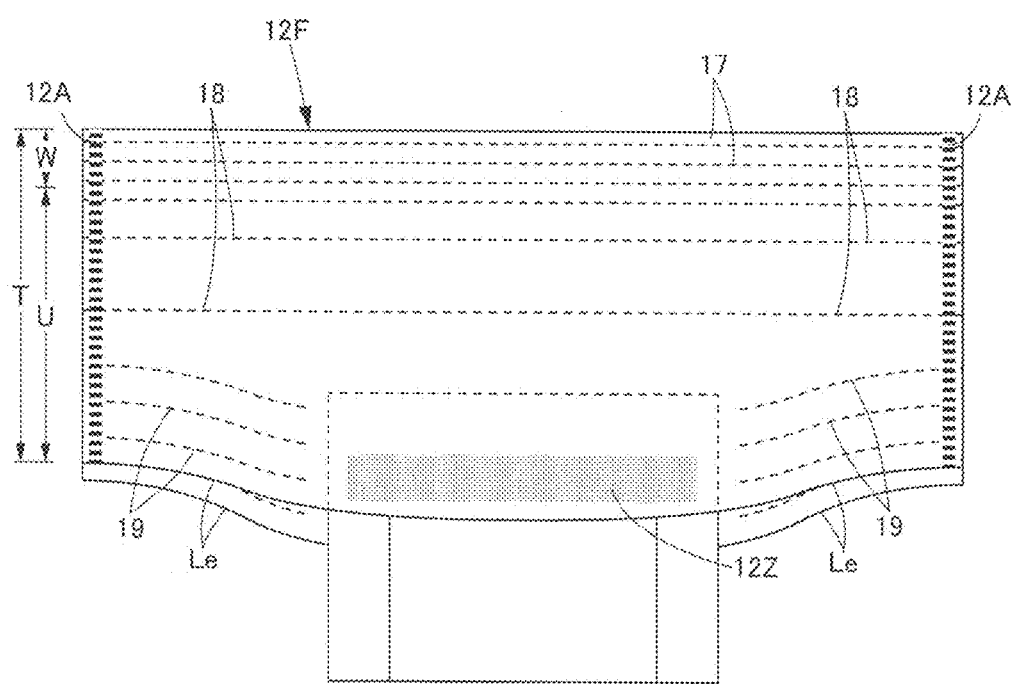
FIG. 29 is a front view of the underpants-type disposable diaper in the open state (extended state in the crotch side)
Figure 30:
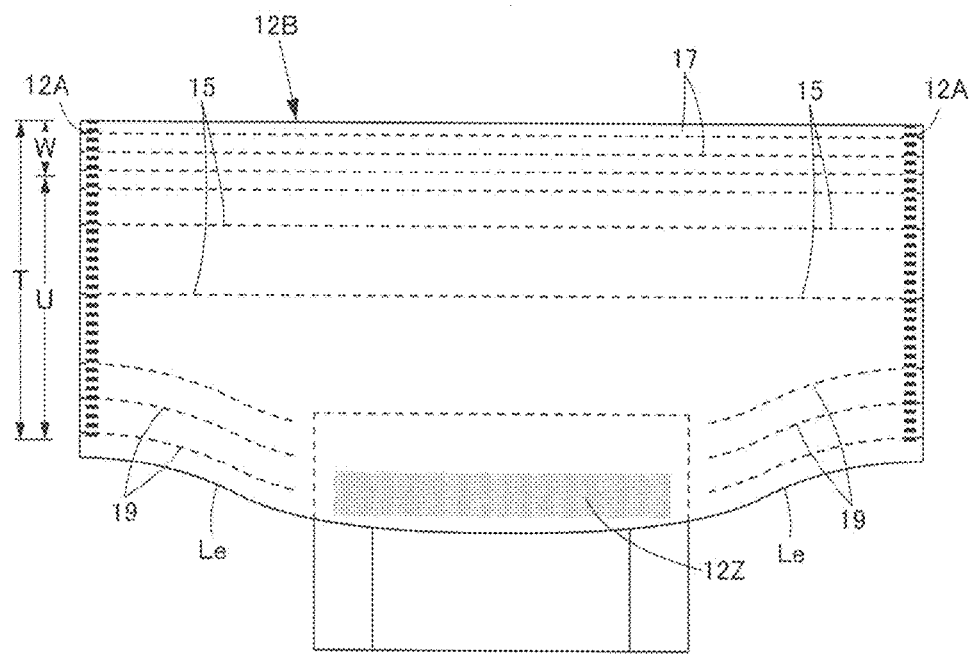
FIG. 30 is a rear view of the underpants-type disposable diaper in the open state (extended state in the crotch side)

FIGS. 23 and 24 illustrate a producing flow of an underpants-type disposable diaper of the second form. A method of producing the second form has a separation portion forming step 310 for intermittently forming separation portions 80 in the MD direction with a slitter device or the like, instead of the folding step 304 in the method of producing the first form descried above. The method of producing the second form differs from that of the first form in that in the inner body attachment step 305, the inner body 200 is joined to the ventral side outer body 12F and the dorsal side outer body 12B at the side closer to the center in the CD direction than to the separation portions 80 to form the inner body joined sections 12Z. Since other details are similar to the first producing method, a description is intentionally omitted.

<Third Form of an Underpants-Type Disposable Diaper>

A third form applies the extensible structure described in Patent Document 4, instead of the extensible structure with the folded part 12W in the first form. More specifically, as illustrated in FIGS. 25 to 30, the dorsal side and ventral side outer body 12F having extensibility at least in the front-back direction, the length in the front-back direction of the side closer to the waist side than to the inner body joined sections 12Z is extensible to the crotch side.

With the extensible structure of the outer bodies 12F and 12B configured with such extensible materials, edges Le of leg openings positioned in the lateral side of the inner body 200 of the outer bodies 12F and 12B obliquely face up to the side edge portions when the diaper is worn, and fit well around wearer's buttocks or the groin region. In addition, the third form can be realized only by changing the sheet materials 12S and 12H. Furthermore, if the outer bodies 12F and 12B are structured to have elastic extensibility in the front-back direction, the contraction force acts along the edges Le of the leg openings in the oblique direction. Thus, the edges Le of the leg openings closely fit around the wearer's buttocks or the groin region.

Note that the extensible structure of the third form can also be adopted in combination with the first form or the second form.

The third form is basically similar to that described in Patent Document 4, except that the portion closer to the waist side than to the inner body joined sections 12Z of the inner body 200 can be moved to the crotch side. Since details such as materials, variants, and the like are similar to those described in Patent Document 4, a description thereof is intentionally omitted. In addition, in the third form, a structure for prevention of inner body movement of the fourth form to be described later is adopted, and the length of the inner body 200 is shorter. Also in the third form, however, the length of the inner body 200 can be made similar to the first form.

<Method of Producing the Third Form>

Figure 31:
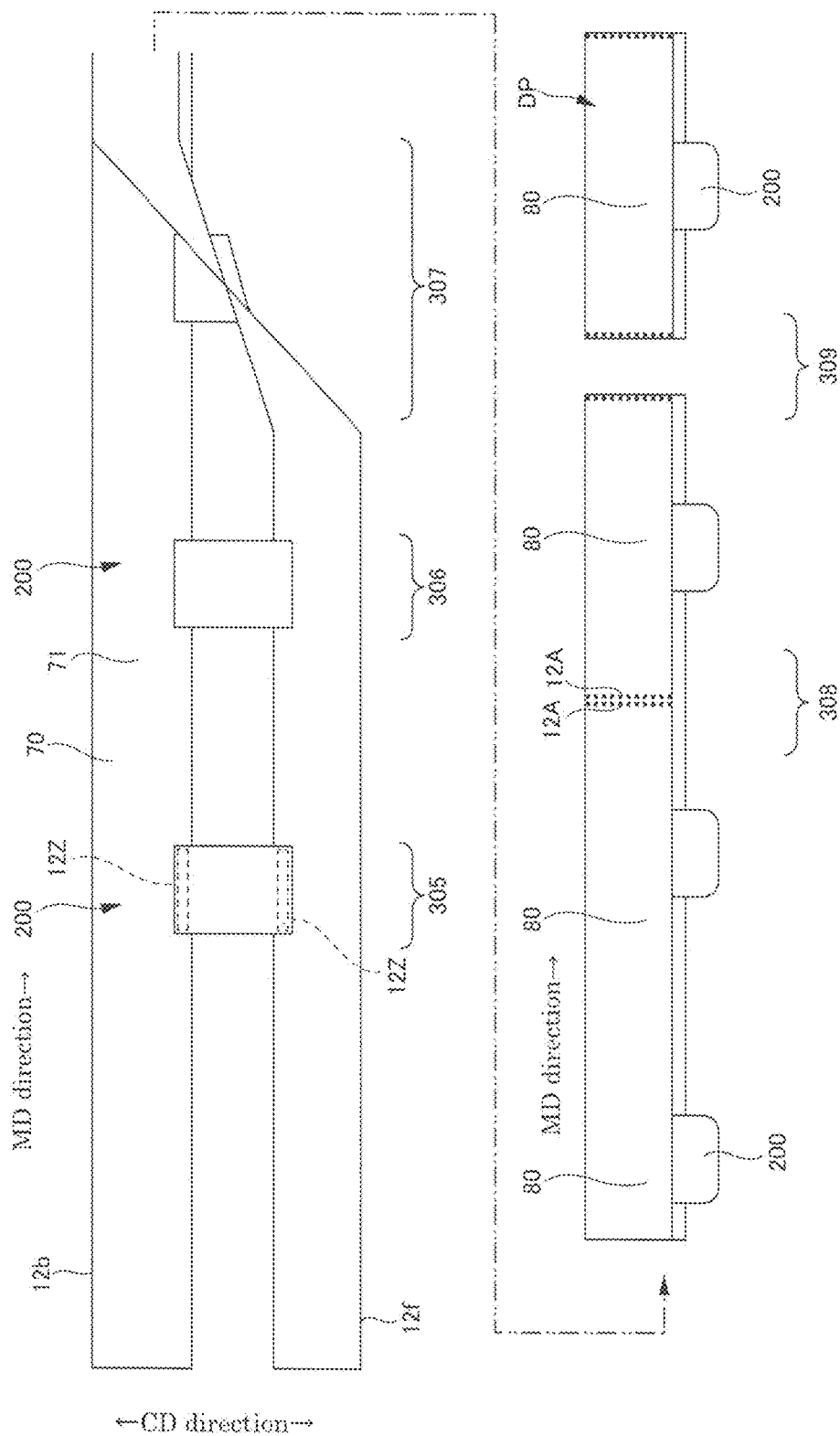
FIG. 31 is a planar view showing a producing flow of the underpants-type disposable diaper.

FIGS. 23 and 31 illustrate a producing flow of an underpants-type disposable diaper of the third form, which differs from the first form in that the folding step 304 of the first form described above is omitted and a material having extensibility at least in the CD direction is supplied as a belt-like sheet materials 12H and 12S in the resilient member attachment step 301, and that in the inner body attachment step 305, a shorter inner body from the edge of the ventral side outer body 12F at the center side in the CD direction to the edge of the dorsal side outer body 12B at the center side in the CD direction is joined to form inner body joined sections 12Z. Since other details are similar to the first producing method, a description is intentionally omitted. Instead of supplying a material having extensibility as the sheet materials 12H and 12S, it is possible to supply a net-like resilient and elastic member and sandwich the net-like resilient and elastic member in the extended state in the MD direction and the CD direction between the sheet materials 12H and 12S.

<Fourth Form of an Underpants-Type Disposable Diaper>

The first form is configured such that the moving portion of the inner body 200 is held down by the pressing belt 70. Instead of this configuration, a form is also proposed in which the inner body 200 can be only extended to the crotch side edge portion of the outer bodies 12F and 12B on the outer bodies 12F and 12B side having the extensible structure, as in the dorsal side of the second form and in both the dorsal side and the ventral side of the third form. Even by shortening a moving portion other than the inner body joined sections 12Z in this manner, it is also possible to prevent unintentional deformation such as bend and turn-up of the moving portion. In particular, a structure in which length of the dorsal side outer body 12B side of the inner body 200 is short is suitable for a product that requires less absorption performance on the dorsal side, such as training pants for infants and incontinence pants for male users.

<Fifth Form of an Underpants-Type Disposable Diaper>

Figure 32:
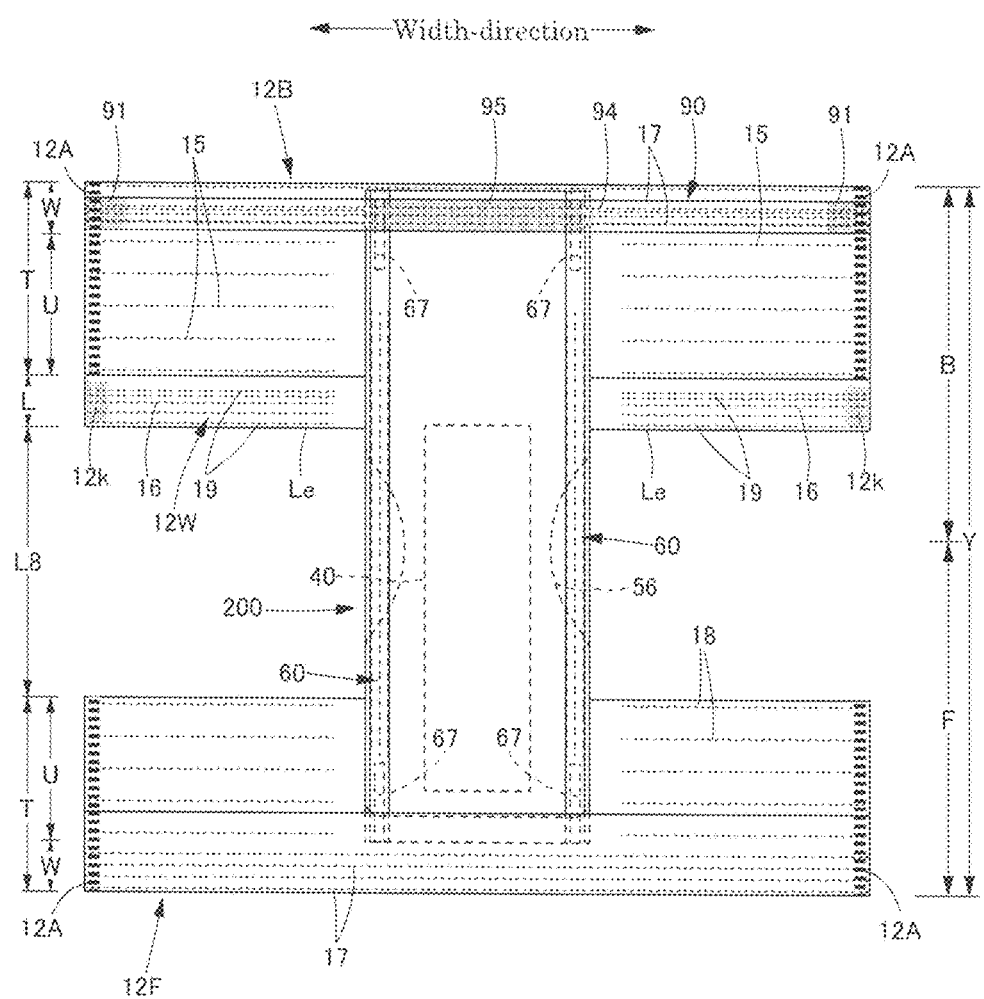
FIG. 32 is a planar view of an inner surface of an underpants-type disposable diaper in the open state.

The first form is configured such that the moving portion of the inner body 200 is held down by the pressing belt 70. Instead of this configuration, as illustrated in FIG. 32, a form is also proposed in which a connecting belt 90 of a similar structure to the pressing belt 70 is extended across the waist side end of the inner body 200 in the width direction, portions (preferably both ends) positioned at both sides of the moving portion of the inner body 200 in the width direction thereof being fixed to the dorsal side outer body 12B with a hot-melt adhesive or the like, and the waist side end of the moving portion of the inner body 200 being connected to the connecting belt 90 with the hot-melt adhesive or the like. Reference sign 91 indicates the portion of the connecting belt 90 fixed to the dorsal side outer body 12B and reference sign 95 indicates the portion fixed to the inner body 200. In addition, reference sign 95 indicates resilient and elastic members. While the connecting belt 90 in the illustrated form is provided, passing over the inner body 200, the connecting belt 90 may pass between the moving portion of the inner body 200 and the outer bodies 12F and 12B.

Figure 33:
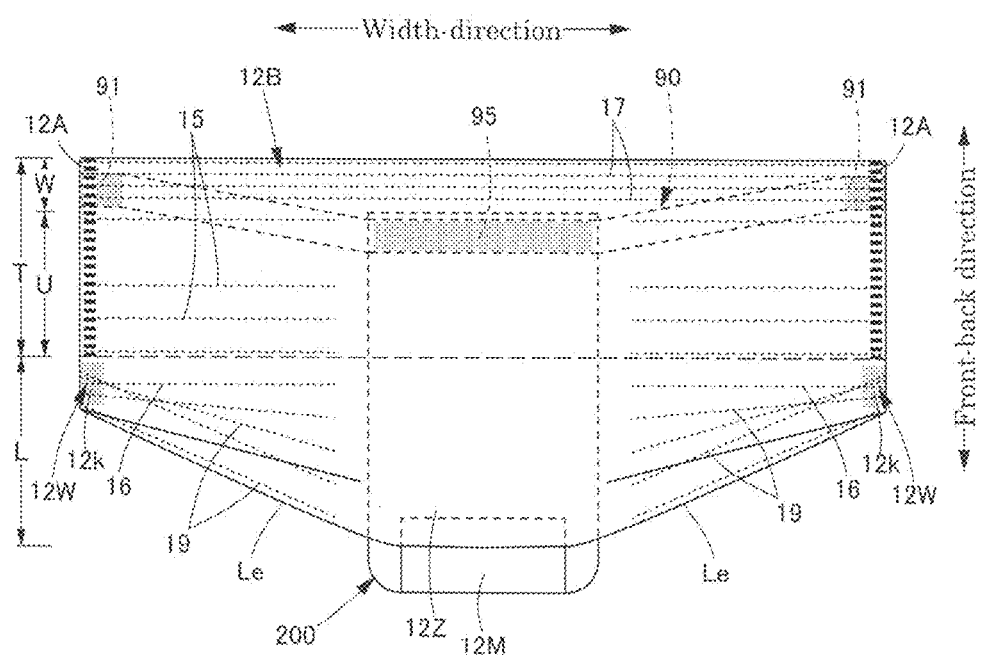
FIG. 33 is a rear view of the underpants-type disposable diaper in the open state (extended state in the crotch side)

With such a connecting belt 90 provided, as illustrated in FIG. 33, when the diaper is worn, the connecting belt 90 sags down as the moving portion of the inner body 200 moves towards the crotch side. However, since movement in the width direction is limited to almost the center in an extent allowed by looseness or sag of the connecting belt 90, the moving portion of the inner body 200 can be prevented from moving unnecessarily or excessively, thereby enabling prevention of unintentional deformation such as bend and turn-up of the moving portion of the inner body 200.

Note that the connecting belt 90 of the fifth form can also be adopted in combination with the pressing belt 70 of the first form or the like. In addition, although it is assumed in the illustrated form that this form is applied to the extensible structure of the first form, it can also be applied to the extensible structure of the second form or the third form.

<Sixth Form of an Underpants-Type Disposable Diaper>

Figure 34:
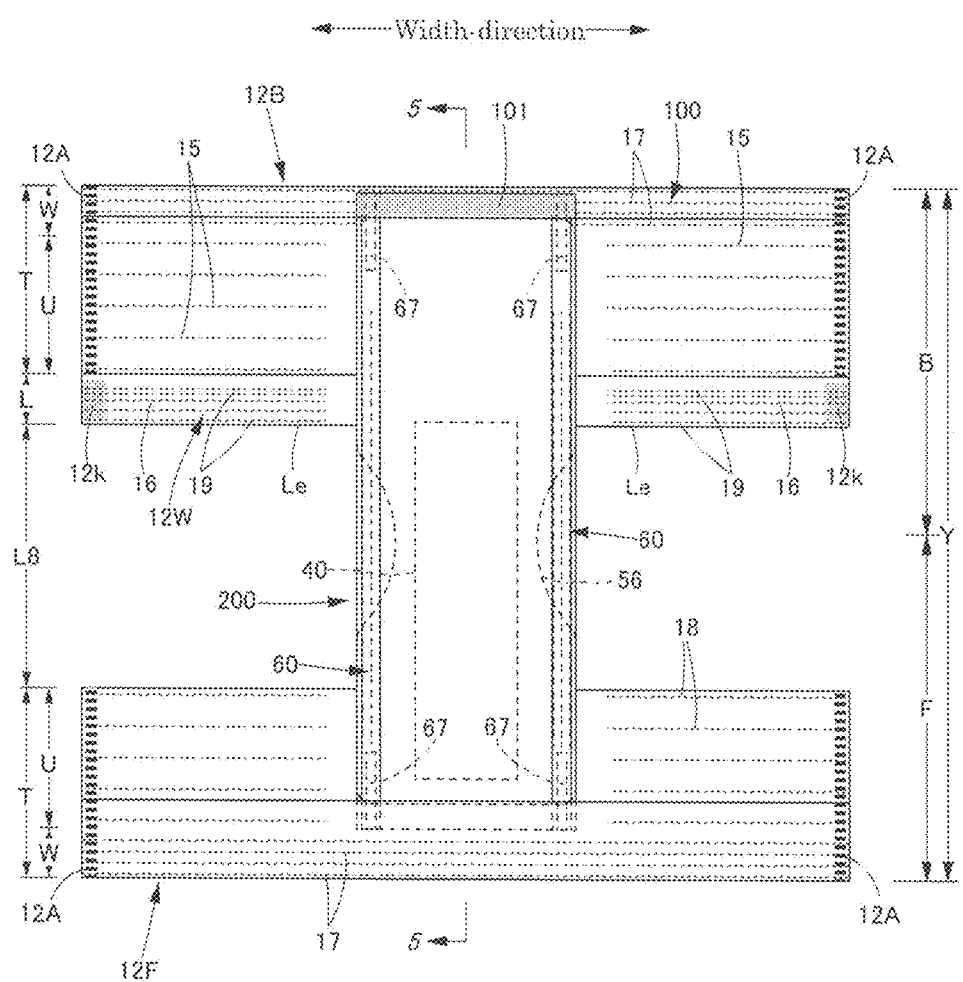
FIG. 34 is a planar view of an inner surface of an underpants-type disposable diaper in the open state.
Figure 35:
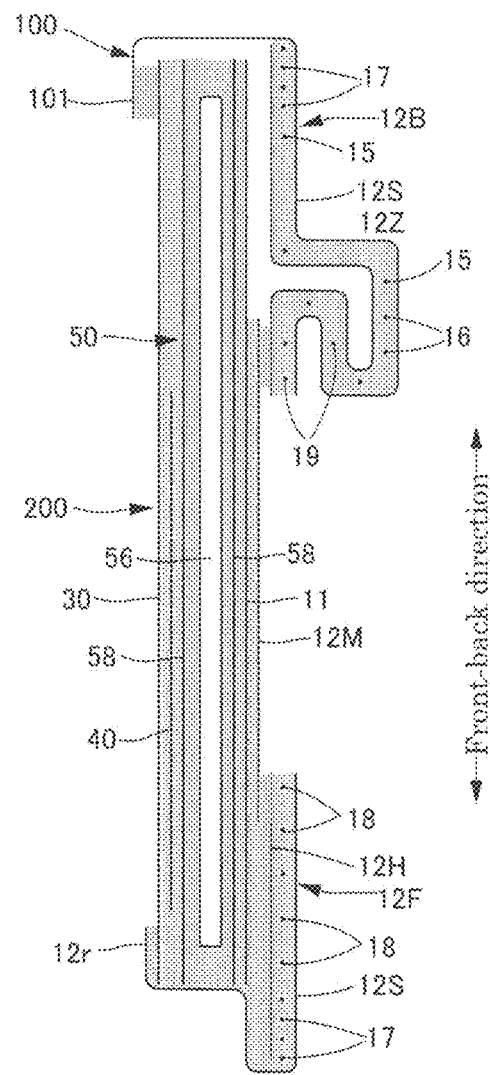
FIG. 35 is a cross-sectional view of FIG. 34 taken along line 5-5.

The first form is configured such that the moving portion of the inner body 200 is held down by the pressing belt 70. Instead of this configuration, as illustrated in FIGS. 34 and 35, a form is also proposed in which a waist flap 100 protruding from the inner surface of the waist edge portion W of the dorsal side outer body 12B is formed, and a moving portion of the inner body 200 is extended and connected to this waist flap 100 with a hot-melt adhesive or the like. Reference sign 101 indicates the portion of the waist flap 100 fixed to the inner body 200. In the illustrated form, while the waist flap 100 is formed by folding back the outer sheet material 12S, which constitutes the dorsal side outer body 12B, to the inside of the diaper at the waist edge portion W and making the folded part unfixed, the waist flap 100 may also be formed by sticking dedicated sheet materials 12S and 12H.

Figure 36:
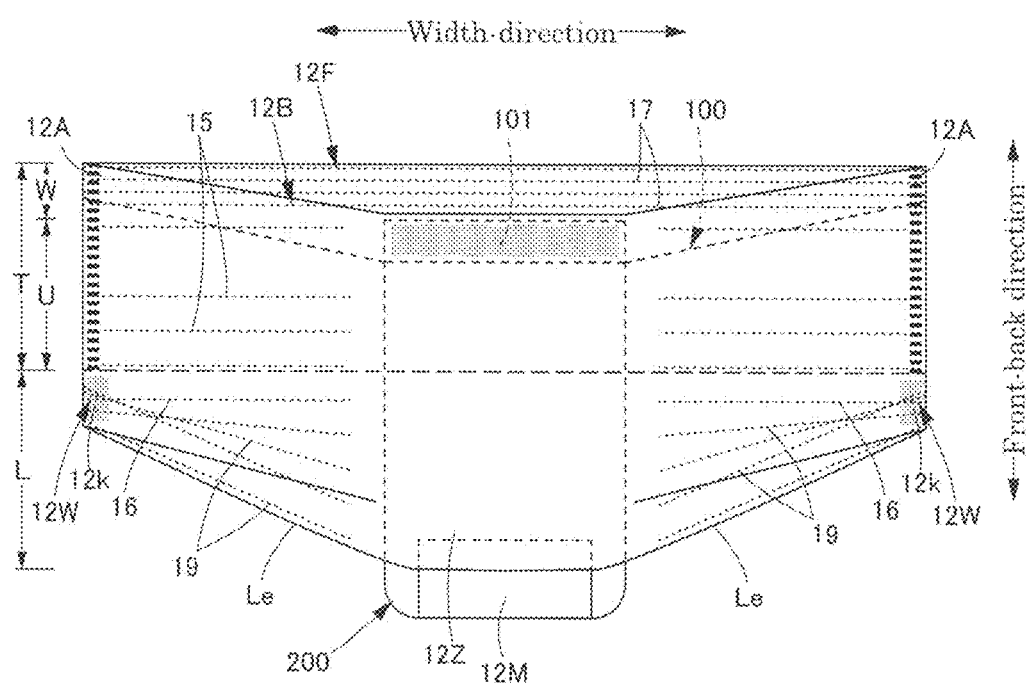
FIG. 36 is a rear view of the underpants-type disposable diaper in the open state (extended state in the crotch side)

If an end of the moving portion of the inner body 200 is connected to the waist flap 100 protruding from the inner surface of the waist edge portion W of the dorsal side outer body 12B, as illustrated in FIG. 36, in the worn state, the waist flap 100 sags down while the dorsal side outer body 12B turns inward, as the moving portion of the inner body 200 moves to the crotch side. However, since movement in the width direction is limited to almost the center in an extent allowed by looseness or sag of the waist flap 100, the moving portion of the inner body 200 can be prevented from moving unnecessarily or excessively, thereby enabling prevention of unintentional deformation such as bend and turn-up of the moving portion of the inner body 200. Furthermore, if the ventral side outer body 12F is extensible, the shape of the waist flap 100 sagging down while the center of the ventral portion of the waist flap 100 in the width direction turns inward as the moving portion of the inner body 200 moves to the crotch side forms a curve along the lower side of a swollen abdominal area of an infant in particular. Thus, the wearing feeling on the ventral side, in particular, is good.

Note that the sixth form can also be adopted in combination with the pressing belt 70 of the first form or the connecting belt 90 of the fifth form. In addition, in the illustrated form, although it is assumed that this form is applied to the extensible structure of the first form, it can also be applied to the extensible structure of the second form or the third form.

<Seventh Form of an Underpants-Type Disposable Diaper>

Figure 37:
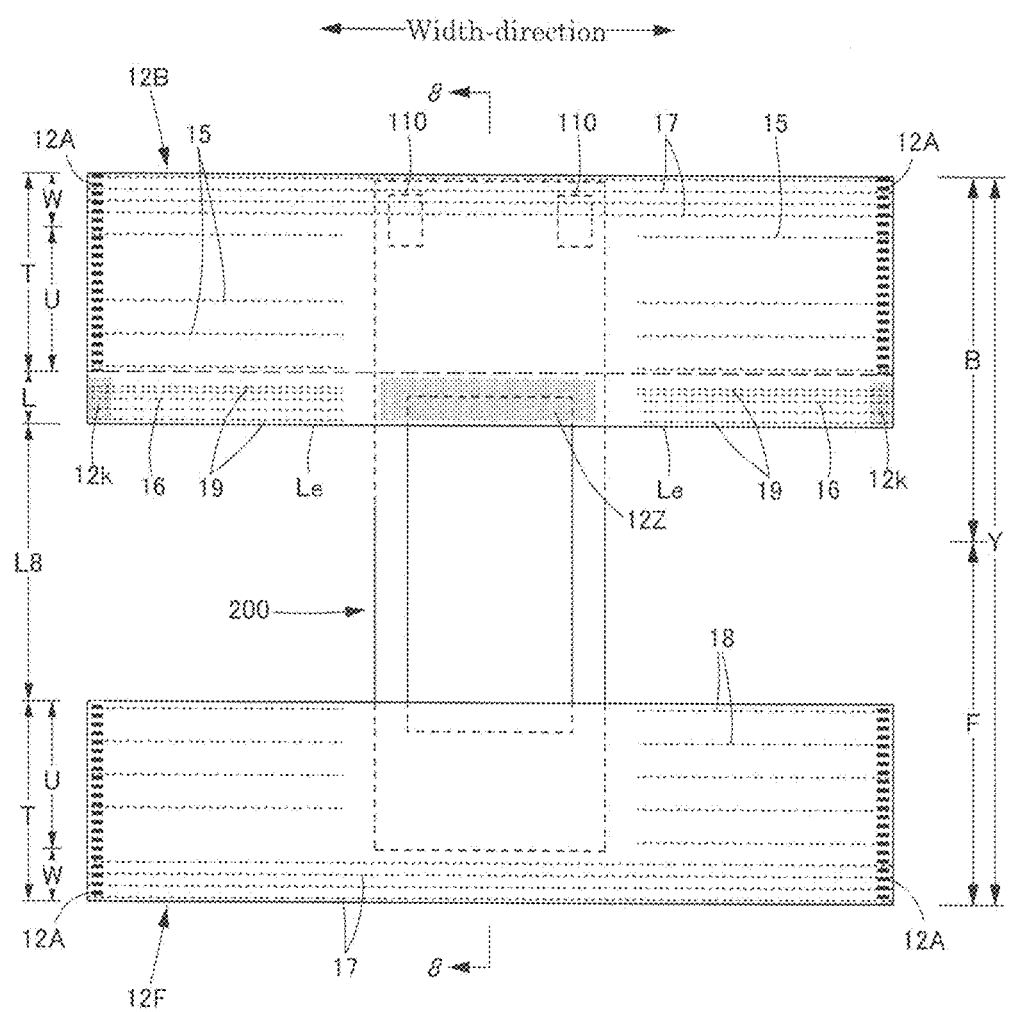
FIG. 37 is a planar view of the underpants-type disposable diaper in the open state.
Figure 38:
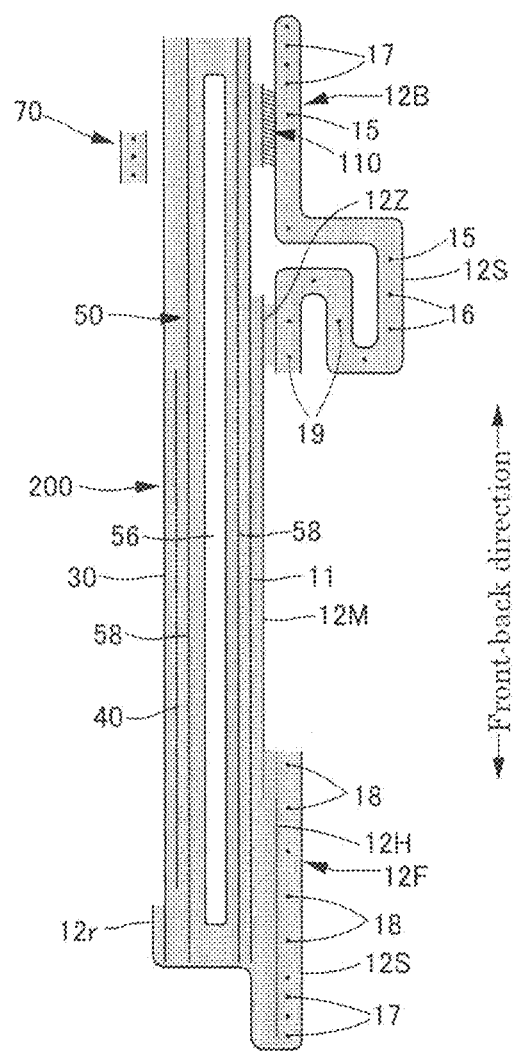
FIG. 38 is a cross-sectional view of FIG. 37 taken along line 8-8.

The first form is configured such that the moving portion of the inner body 200 is held down by the pressing belt 70. Instead of or together with this configuration, as illustrated in FIGS. 37 and 38, a form is also proposed in which a slip stopper 110 whose antislip effect on the crotch direction is weaker than antislip effect on any other direction is provided at a region overlapping the moving portion in the dorsal side outer body 12B capable of extending to the crotch side.

As such a slip stopper 110, for example, a hook material (hook member) of a mechanical fastener (hook-and-loop fastener) having pins tilted to the crotch portion side can be used. With such a slip stopper 110 provided, while extension of the dorsal side outer body 12B is allowed, the moving portion of the inner body 200 can be held down so as not to move unnecessarily or excessively, thereby enabling prevention of unintentional deformation such as bend and turn-up of the moving portion of the inner body 200.

Note that the seventh form can be adopted in combination with the pressing belt 70 of the first form or the like, the connecting belt 90 of the fifth form, or the free edge portions of the sixth form. In addition, in the illustrated form, although it is assumed that this form is applied to the extensible structure of the first form, it can also be applied to the extensible structure of the second form or the third form.

Descriptions of the Terms Used Herein

Unless otherwise specified herein, the terms used herein have the meanings described below.

"front-back (vertical) direction" refers to the direction linking the ventral side (front side) and the dorsal side (back side), and the "width direction" refers to the direction (right-left direction) orthogonal to the front-back direction. The "up-down direction" refers to the direction that becomes orthogonal to the waist direction when the diaper is worn, that is, when the diaper is folded into two at the crotch portion such that the front panel and the back panel are overlapped at the both sides, in other words, the direction linking a waist opening and a crotch portion.

The "extension ratio" refers to a value with respect to 100% representing the natural length.

The "gel strength" is measured in such a manner as described below. That is, a high-absorbent polymer of 1.0 g is added to an artificial urine of 49.0 g (urea: 20 wt %, salt: 8 wt %, calcium chloride dihydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

The "basis weight" is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$.

If there is no description on environmental conditions in testing or measurements, the testing or the measurements shall be conducted in a test room or within a device under a normal state (a place of test shall be at temperatures of 20±5° C. and relative humidity of 60% or less).

INDUSTRIAL APPLICABILITY

The present invention can be utilized in underpants-type disposable diapers.

REFERENCE SIGNS LIST

L Intermediate portion
Le Edge of leg opening
T Waist portion
U Lower waist portion
W Waist edge portion
11 Liquid impervious sheet
12A Side seal portion
12B Dorsal side outer body
12F, 12B Outer body
12F Ventral side outer body
12H Inner sheet material
12M Crotch portion cover sheet
12S, 12H Sheet material
12S Outer sheet material
12W Folded part
12Z Inner body joined section
12b Dorsal side elastic belt
12c Intermediate portion in a CD direction
12d Separation portion
12e Edge portion sheet material
12f Ventral side elastic belt
12w Overlapped portion
15 to 19 Elongated resilient and elastic member
16 Intermediate resilient and elastic member
17 Waist edge resilient and elastic member
19 Oblique resilient and elastic member
30 Top sheet
50 Absorbent element
56 Absorber
58 Wrapping sheet
60 Three-dimensional gather
62 Gather sheet
70 Pressing belt
80 Separation portion
90 Connecting belt
100 Waist flap
110 Slip stopper
200 Inner body
301 Resilient member attachment step
302 Resilient member cutting step
303 Center slit step
304 Folding step
305 Inner body attachment step
306 Pressing belt attachment step
307 Folding up step
308 Side part joining step
309 Cutoff step
310 Separation portion forming step

The invention claimed is:

1. An underpants-type disposable diaper, comprising:
an outer body having a ventral side outer body and a dorsal side outer body, side edge portions of the ventral side outer body and side edge portions of the dorsal side outer body being joined at both sides in a width direction to form a waist opening; and
an inner body extended from a central area of the ventral side outer body in the width direction to a central area of the dorsal side outer body in the width direction so as to pass through a wearer's crotch,
wherein a crotch side edge portion of a central portion of at least one of the ventral side outer body and the dorsal side outer body in the width direction is joined with the inner body to form an inner body joined section, and
a part of the at least one of the ventral side outer body and the dorsal side outer body disposed at the crotch side edge portion of the at least one of the ventral side outer body and the dorsal side outer body is folded in a front-back direction once or a few times in a zigzag manner,
both lateral side end portions of the crotch side edge portion are fixed in a folded state to constitute non-unfolded parts,
a part between the non-unfolded parts is unfixed and unfolded, so that a folded part is formed,
the inner body is joined to a portion of the folded part disposed closer to a forward edge than to a fold closest to the forward edge to form the inner body joined section, and
the folded part is configured to unfold so that a length in the front-back direction of a side of the at least one of the ventral side outer body and the dorsal side outer body closer to a waist than to the inner body joined section is extensible to a crotch side, and
a portion of the inner body disposed closer to the waist than to the inner body joined section can be moved to the crotch side, relative to the at least one of the ventral side outer body and the dorsal side outer body,
a length in the front-back direction of a rectangular section of the at least one of the ventral side outer body and the dorsal side outer body is not extended to the crotch side before the diaper is worn, and
the length in the front-back direction of the side of the at least one of the ventral side outer body and the dorsal side outer body closer to the waist than to the inner body joined section is naturally extensible to the crotch side when the diaper is worn, so that edges of leg openings in the outer body positioned at lateral sides of the inner body obliquely face up to the side edge portions.

2. The underpants-type disposable diaper according to claim 1, wherein
the at least one of the ventral side outer body and the dorsal side outer body has extensibility at least in the front-back direction so that the length in the front-back direction of the side of the at least one of the ventral side outer body and the dorsal side outer body closer to the waist than to the inner body joined section is extensible to the crotch side.

3. The underpants-type disposable diaper according claim 1, wherein the inner body is extended only to the crotch side edge portion of the at least one of the ventral side outer body and the dorsal side outer body.

4. The underpants-type disposable diaper according to claim 1, wherein
the inner body has a moving portion extended on a side of the inner body closer to the waist than to the inner body joined section on the at least one of the ventral side outer body and the dorsal side outer body, and
a pressing belt is provided so as to extend across the inner body in the width direction of the at least one of the ventral side outer body and the dorsal side outer body closer to the waist than to the inner body joined section, and so as to have portions, which are positioned at both sides of the moving portion of the inner body in the width direction to be fixed, and a portion, which is passed over the moving portion of the inner body to be unfixed.

5. The underpants-type disposable diaper according to claim 1, wherein the inner body has a moving portion extended on a side of the inner body closer to the waist than to the inner body joined section on the at least one of the ventral side outer body and the dorsal side outer body, and a connecting belt is provided so as to extend across a waist side end portion of the inner body in the width direction of the at least one of the ventral side outer body and the dorsal side outer body closer to the waist than to the inner body joined section, and so as to have portions, which are positioned at both sides of the moving portion of the inner body in the width direction to be fixed, and the waist side end portion of the inner body is connected to the connecting belt.

6. The underpants-type disposable diaper according to claim 1, wherein the inner body has a moving portion extended on a side of the inner body closer to the waist than to the inner body joined section on the at least one of the ventral side outer body and the dorsal side outer body, and a waist flap is provided so as to protrude from an inner surface of a waist edge portion of the at least one of the ventral side outer body and the dorsal side outer body, and the moving portion of the inner body is extended and connected to the waist flap.

7. The underpants-type disposable diaper according to claim 1, wherein the inner body has a moving portion extended in a side of the inner body closer to the waist than to the inner body joined section in the at least one of the ventral side outer body and the dorsal side outer body, and on a site overlapping the moving portion of the at least one of the ventral side outer body and the dorsal side outer body, a slip stopper is provided to produce a weaker antislip effect in a direction toward the crotch than in any other directions.

8. An underpants-type disposable diaper, comprising:

an outer body having a ventral side outer body and a dorsal side outer body, side edge portions of the ventral side outer body and side edge portions of the dorsal side outer body being joined at both sides in a width direction to form a waist opening; and an inner body extended from a central area of the ventral side outer body in the width direction to a central area of the dorsal side outer body in the width direction so as to pass through a wearer's crotch, wherein a crotch side edge portion of a central portion of at least one of the ventral side outer body and the dorsal side outer body in the width direction is joined with the inner body to form an inner body joined section, and on the at least one of the ventral side outer body and the dorsal side outer body closer to a waist than to the inner body joined section, a separation portion composed of a slit or an elongated opening is provided so as to extend in the width direction from one side to another side of a center in the width direction, a portion disposed at a crotch side of the separation portion is deformed to separate in relation to a portion disposed at a waist side of the separation portion to the crotch side so that to length in a front-back direction of a side of the at least one of the ventral side outer body and the dorsal side outer body closer to the waist than to the inner body joined section is extensible to the crotch side, and a portion of the inner body disposed closer to the waist than to the inner body joined section can be moved to the crotch side, relative to the at least one of the ventral side outer body and the dorsal side outer body, and a length in the front-back direction of a rectangular section of the at least one of the ventral side outer body and the dorsal side outer body is not extended to the crotch side before the diaper is worn, and the length in the front-back direction of the side of the at least one of the ventral side outer body and the dorsal side outer body closer to the waist than to the inner body joined section is extensible to the crotch side when the diaper is worn so that edges of leg openings in the outer body positioned at lateral sides of the inner body obliquely face up to the side edge portions.

* * * * *